(12) United States Patent
Gross et al.

(10) Patent No.: US 7,998,117 B2
(45) Date of Patent: Aug. 16, 2011

(54) DRUG DELIVERY DEVICE

(75) Inventors: Joseph Gross, Israel (IL); Izrail Tsals, Newton, PA (US); Gilad Lavi, Rishon Letzion (IL); Gil Yigal, Gan Yavne (IL); Ehoud Carmel, Kiryat-Ono (IL)

(73) Assignee: Elan Pharma International Limited, Monksland, Athlone, County Westmeath (IE)

( * ) Notice: Subject to any disclaimer, the term of this patent is extended or adjusted under 35 U.S.C. 154(b) by 40 days.

(21) Appl. No.: 12/121,545

(22) Filed: May 15, 2008

(65) Prior Publication Data

US 2008/0215005 A1    Sep. 4, 2008

Related U.S. Application Data

(62) Division of application No. 10/461,040, filed on Jun. 13, 2003, now Pat. No. 7,384,413, which is a division of application No. 09/275,464, filed on Mar. 23, 1999, now Pat. No. 6,595,956.

(60) Provisional application No. 60/079,047, filed on Mar. 23, 1998.

(51) Int. Cl.
*A61M 37/00* (2006.01)

(52) U.S. Cl. ........................ 604/141; 604/131

(58) Field of Classification Search ................ 604/131, 604/132, 133, 143, 145–147, 151, 140–141, 604/153–154, 207–209
See application file for complete search history.

(56) References Cited

U.S. PATENT DOCUMENTS

| | | | |
|---|---|---|---|
| 3,802,430 | A | 4/1974 | Schwebel et al. |
| 4,150,672 | A | 4/1979 | Whitney et al. |
| 4,320,757 | A | 3/1982 | Whitney et al. |
| 4,886,499 | A | 12/1989 | Cirelli et al. |
| 5,024,656 | A | 6/1991 | Gasaway et al. |
| 5,370,630 | A | 12/1994 | Smidebush et al. |
| 5,785,688 | A | 7/1998 | Joshi et al. |
| 5,814,020 | A | 9/1998 | Gross |
| 5,860,957 | A | 1/1999 | Jacobsen et al. |
| 6,045,534 | A | 4/2000 | Jacobsen et al. |
| 6,595,956 | B1 * | 7/2003 | Gross et al. .............. 604/141 |
| 7,384,413 | B2 * | 6/2008 | Gross et al. .............. 604/141 |

FOREIGN PATENT DOCUMENTS

| | | |
|---|---|---|
| WO | 9323096 A1 | 11/1993 |
| WO | 9532013 A1 | 11/1995 |
| WO | 9710012 A1 | 3/1997 |

* cited by examiner

*Primary Examiner* — Theodore J Stigell
(74) *Attorney, Agent, or Firm* — Fox Rothschild LLP

(57) ABSTRACT

A drug delivery device having a housing containing a gas generator controlled by an electronic controller. The gas generator generates gas into a reciprocable chamber, whereby reciprocation of the chamber causes a lever to reciprocate a pawl, and this action causes a ratchet to undergo incremental advancement. The device may also be provided with manual control for delivering a bolus dose of drug when necessary.

11 Claims, 18 Drawing Sheets

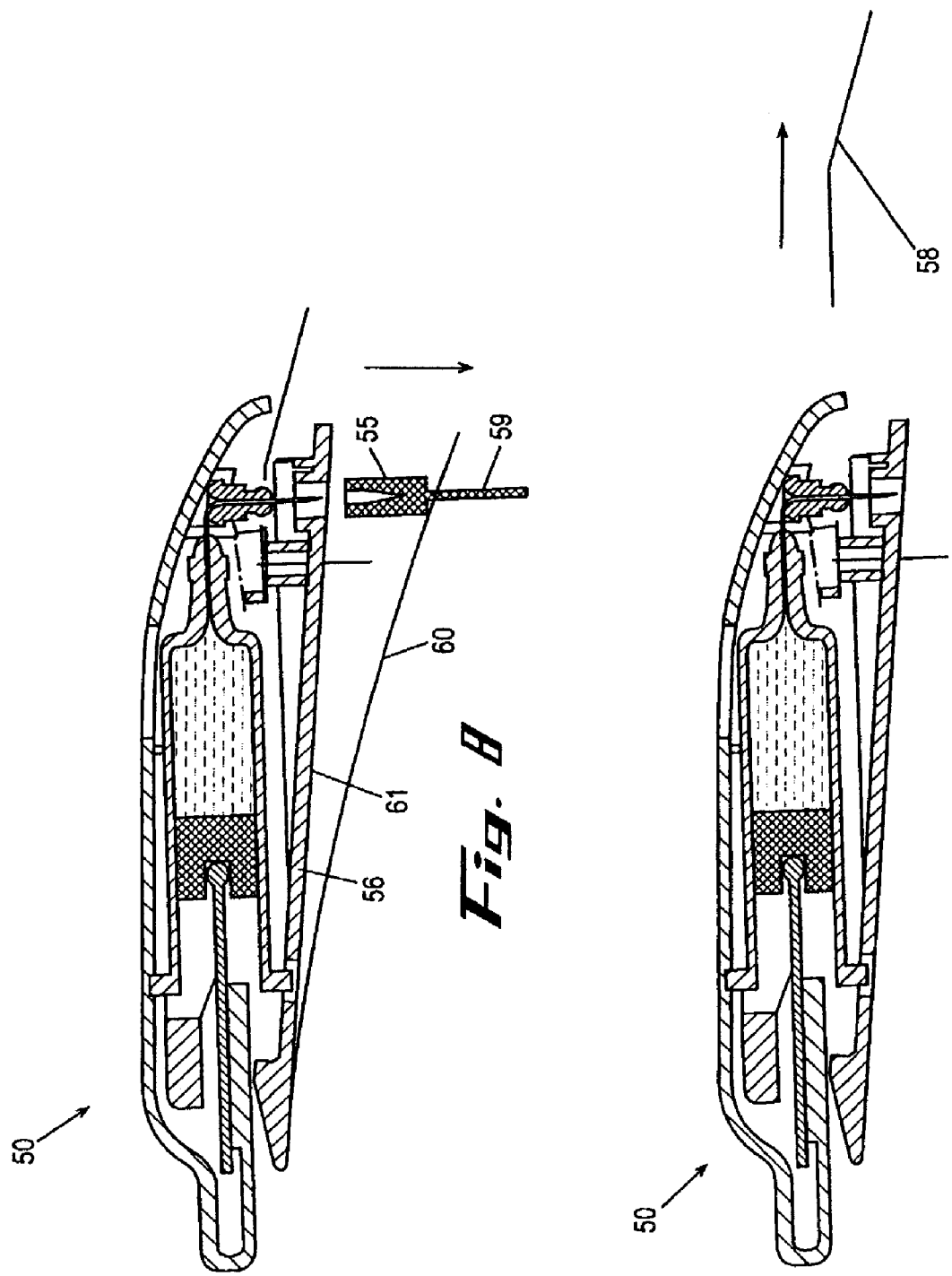

DRUG DELIVERY DEVICE

CROSS-REFERENCE TO RELATED APPLICATIONS

This application is a division of U.S. patent application Ser. No. 10/461,040, filed Jun. 13, 2003, now U.S. Pat. No. 7,384,413, which is a division of U.S. patent application Ser. No. 09/275,464, filed Mar. 23, 1999, now U.S. Pat. No. 6,595,956, which claims priority to U.S. Provisional Patent Application No. 60/079,047, filed Mar. 23, 1998, the entire contents of these applications being hereby incorporated by reference in their entirety.

This invention relates to drug delivery devices, and in particular to portable devices designed to be carried by a patient during normal activities.

BACKGROUND OF THE INVENTION

A number of drug delivery devices are known in which medicament is driven from a reservoir, under the action of a driving mechanism, through a needle and into the skin of a patient. A problem with known devices is that the delivery rate accuracy suffers when the volume of drug is small. Such inaccuracies arise in many cases from the driving mechanisms employed which give rise to variations in delivery rates. For example, where a gas is generated to drive a plunger in a cartridge or vial, the volume of gas depends in part on the temperature of the environment. The variation in volume will also depend on the total amount of gas already present in the chamber.

The reason that gas generation is preferred over mechanical driving mechanisms is that the design of gas generating cells, such as electrolytic cells' is extremely simple when compared to mechanical equivalents, and this provides significant advantages in terms of reliability and cost-effectiveness. Systems are known in which a mechanically driven ratchet is used to incrementally deliver fixed amounts of medicament, but such systems can be expensive to manufacture. In particular, the accuracy of delivery of small amounts of drug depends on the manufacturing tolerances of the ratchet mechanism. For mass-produced, moulded, cut or pressed ratchets, the tolerances may not be sufficiently accurate to deliver the required small volumes, which means that more expensive manufacturing techniques are required to obtain the necessary tolerances. Such considerations are particularly important if the devices are intended to be disposable, in which case a low unit cost is required without compromising accuracy or reliability or system performance.

A problem with gas driven mechanisms, however, is that it is extremely difficult to ensure that a gas chamber is leakproof without taking elaborate manufacturing and quality control precautions. Even if a leak is minor and relatively slow, this poses a real problem when the mechanism is supposed to accurately deliver small volumes over extended timespans. Thus, for gas generation systems, it is preferred to design a system that is leak free (which is costly and typically more complex) or provide a system that functions accurately in spite of minor or relatively slow leaks. In the alternative, gas generation may not be suitable for lower delivery rates. As mentioned above, mechanical equivalents having the required precision (e.g. clockwork mechanisms) are overly expensive and complex for incorporation into inexpensive devices which may be disposable.

For many drug delivery regimes, it is desirable to provide both steady state delivery ("basal delivery") and instantaneous bursts of drug ("bolus delivery") as required. In particular, in patient controlled analgesia or PCA, it may be advantageous to provide a continuous basal infusion of drug for chronic pain treatment, supplemented to a certain extent by bolus delivery. The bolus delivery would be activated by the patient to deal with increased temporary pain levels ("break-through pain"), with safeguards being incorporated to prevent overdosing.

Another area in which precisely controlled dosing can be particularly indicated is in chronotherapeutic drug delivery, in which the drug delivery rate varies over time. Most notably, diurnal or circadian rhythms cause variations in the amounts of certain drugs required by a patient during a 24-hour period. This is most notably required to combat variations in disease and/or condition effects throughout a 24-hour cycle.

For example, hypertension crises, angina, and sudden cardiac death are most likely to occur in the morning, whereas sickle cell crises and perforated ulcer crises are most likely to occur in the afternoon. The concept of chronotherapeutics is discussed in more detail in an article by Smolensky & Labrecque, *Pharmaceutical News* 4, No. 2, 1997, pp. 10-16. The discussion in this article is principally in terms of conventional oral dosing of drugs to take account of chronotherapeutic variations in drug uptake, effects, and requirements, but many of the principles are applicable to other delivery routes. Circadian rhythm applications would also apply to hormonal therapies.

Accordingly there is a need to provide a drug delivery device capable of regulating drug delivery dosages to provide increased dosages at the times when such dosages are more likely to be required. This gives rise to a need for a device in which the delivery rate is accurately controllable over a wide range of delivery rates. In general, devices which are designed to deliver small amounts of drug are not particularly suitable for high drug delivery rates without being specifically adapted in this regard, and vice versa. Moreover there is a need to provide such a device that is relatively compact so that it is fixed to the user during use and disposed of when the treatment is finished. Such a device must be also relatively inexpensive to manufacture yet maintain accurate and reliable delivery rates The present invention aims to provide improved drug delivery devices in which smaller volumes of liquid can be delivered more accurately than in prior art devices, thereby giving rise to overall more controlled delivery rates. The invention also aims to provide such devices which additionally allow higher delivery rates to be provided on demand, up to and including bolus delivery. Moreover, the present invention provides for a drug delivery device wherein the technology used to provide for accurate delivery rates is relatively easy and inexpensive to manufacture. Further, the present invention employs designs for the gas generating system and delivery system so that space within the device is minimised and parts used within the device are easy and inexpensive to manufacture while maintaining high tolerances. In addition, the present invention provides for a certain amount of gas leakage while delivering accurate dosages. This eliminates the need for costly sealing devices and systems which increase cost and decrease reliability in the event of gas leakage.

SUMMARY OF THE INVENTION

The invention provides a drug delivery device having a housing containing a drug reservoir, and means for facilitating the expulsion of drug from the drug reservoir. The device also includes a mechanism in communication with the facilitation means, that incrementally advances and thereby drives the drug from the reservoir, and a member associated with the mechanism to cause the incremental advancement of the mechanism as the member moves in a first direction. The device also includes a gas generator located within the housing and operable to expand in a chamber. The member is in transmission relation to the chamber. In operation, the member is driven by the movement of the chamber to advance the mechanism and thereby drive the drug from the reservoir in incremental fashion.

Preferably, the mechanism in communication with the facilitation means comprises a ratchet.

Further, preferably, the member moves in a reciprocable fashion.

Further, preferably, the movement of the reciprocable member causes the stepwise advancement of the mechanism.

Further, preferably, the reciprocable member is connected to a wall of the chamber, whereby the reciprocation of the reciprocable member is driven by the expansion and contraction of the chamber.

The preferred devices according to the invention take advantage of the reciprocation of a gas generation chamber to effect a stepwise advancement of a ratchet mechanism. Gas generation chambers which expand and contract repeatedly are advantageous over known chambers which simply expand over time. For example, a ratchet which has 100 teeth and is driven by a continuously expanding gas chamber will advance one step for every 1% increase in the chamber volume. According to basic gas laws, a temperature rise of only 3° C. will increase the volume of a gas at room temperature by 1%. Thus, towards the end of the chamber expansion, a temperature rise of 3° C. will drive the ratchet one step forward independently of the gas generation rate. In contrast, a chamber which reciprocates will undergo a full expansion for each stepwise advance of the ratchet mechanism, and a 1% variation in the volume of this chamber will have no material effect on the fact that the chamber will expand fully and advance the ratchet correctly.

For example, a ratchet mechanism which undergoes 100 stepwise advances throughout the emptying of a reservoir. If this ratchet is driven by a continuously expanding gas chamber, a 1% increase in the volume of gas towards the end of the delivery period will advance the ratchet by an (undesired) extra step. Such a 1% expansion occurs with a temperature change of only 3° C. (which is approximately 1% of the room temperature when expressed in kelvins). The situation is worse for devices which require several hundred ratchet advances to ensure the necessary sensitivity for accurate delivery over an extended time period.

In contrast, devices according to the present invention employ a reciprocating chamber which continually expands and contracts. This enables small-volume chambers to be employed such that the difference in volume between the contracted and expanded states is orders of magnitude greater than the change in volume arising from environmental temperature changes. Moreover, by employing a reciprocating chamber, less space is needed for the chamber as the volume at maximum expansion is considerably less that what would be required for a continuously expanding chamber at the maximum volume of expansion.

Preferably, the chamber is elastically biased to revert to a contracted state, and wherein a venting means is provided to enable contraction of the chamber after gas generation has expanded the chamber.

One advantage of using a reciprocity chamber to drive a reciprocating mechanism linked to a ratchet is that there is sufficient amplitude of movement in the reciprocation to advance the ratchet by the required number of steps (in many cases only one step), to ensure that venting is sufficiently thorough to relax the system completely, in order to arrive at a device in which the delivery rate is controlled to a high degree of accuracy.

For example, if the delivery volume is low (equivalent to a single stepwise ratchet advance) every five minutes, then the gas generator can be designed to deliver a sufficient amount of gas within one minute, and then switch off automatically for four minutes. In the first minute, the ratchet will be caused to advance by the required "tooth" (or equivalent), and then the venting means is actuated to relax the system. By the end of four minutes the system will be fully relaxed and the cycle can begin again.

This design automatically compensates for any inaccuracies in the performance of its driving mechanism. Thus, the gas generator can be designed to deliver e.g. 20%±10% more than the required volume of gas (i.e. not a particularly expensive or accurate system), and still to have an extremely accurate delivery for the following reason. If the gas generator generates between 10% and 30% too much gas on each cycle, the ratchet will advance by a single "tooth", but it is equally certain that it will not be pushed to advance by a second tooth. Thus, when the gas generation ceases, a certain amount of controlled overpressure or stress will be present in the system, but the amount of drug delivered will be precisely known. Then when the gas is vented, the overpressure is released and the system returns to equilibrium. Thus, the accuracy of delivery at the end of the five minute cycle is independent of whether the generator generated 10% or 30% too much gas.

It should be noted that the accuracy of the system is controlled by the tolerances of the ratchet mechanism, the timer, the reciprocity chamber, the venting system and the gas generator.

In some embodiments, the venting means is passive and allows escape of gas therethrough when the chamber is pressurised relative to atmospheric pressure. In other embodiments, there is designed to be venting means within the gas generator. Such venting means may connect sub-chambers within the gas generating means. The venting means enables the sub-chambers to increase and decrease pressure therein more efficiently.

In some embodiments, the gas generator is adapted to generate gas at a rate higher than the venting rate. When the gas generator is active, the chamber becomes pressurised and expands, and when the gas generator is inactive, the venting means causes depressurisation and contraction of the chamber. Minor leaks in the system, provided that they are not so serious as to prevent the chamber from fully pressurising, do not have any significant effect on the operation or accuracy of the device. This enables a gas generating system to deliver extremely small volumes of drug in a highly controlled, accurate manner, without employing any elaborate gas generation system, or any special leakproofing of the gas chamber. Also, the gas generation rate should exceed the venting rate so that the error of movement of the reciprocator member errs to the side of excessive pressure rather than too little pressure. If there is insufficient pressure (i.e. caused by the leakage rate exceeding the pressurisation rate, the force needed to move the reciprocating member will be insufficient and the pawl on the ratchet will not move. Thus, the volume of drug will not be advanced through the cartridge and delivered to the user.

In alternative embodiments, the gas pressure of the gas generator is divided between at least two cells. A first cell has a more permeable member and is designed for minimum gas leakage. The first cell also has a controllable vent associated therewith. The vent allows excess gas to escape from the first cell but prevents the escape of gas at a stage in the cycle when the member of the first cell is needed to deflect so as to cause forward movement of the ratchet. The alternative embodiment is also designed so that the latter part of the cycle allows the re-opening of the first cell vent to enable gas therein to quickly escape and cause the member to return to its initial resting position.

In some preferred embodiments, the venting means comprises a permeable or semi-permeable member. Currently one of the most preferred member is a silicone membrane. In another embodiment, there are at least two members with varying permeability. The less permeable material is preferably bromo-butyl, ethylene propylene or EPDM, and the more permeable member is preferably silicone rubber.

Suitably, the mechanism is caused to advance as the chamber undergoes expansion. Alternatively, the mechanism may be caused to advance as the chamber undergoes contraction. While it is possible to employ a mechanism which drives the ratchet forward during both expansion and contraction strokes, it is preferred to employ a single driving stroke (either contraction or expansion) during a reciprocation cycle for lower delivery rates.

Suitably, the member comprises a lever extending between the chamber and the mechanism.

The use of a lever mechanism enables the amplitude of movement of the expanding chamber to be accurately converted to the correct amplitude of movement to drive the ratchet.

In certain preferred embodiments, the mechanism comprises a rigid ratchet element having spaced formations on a surface thereof.

Preferably, the formations have a sawtooth cross section, although the formations may be in the form of grooves on a surface of the rigid ratchet element.

Preferably, the mechanism includes a pawl carried on the member, the pawl being adapted to make ratcheting engagement with the formations on the rigid ratchet element.

Further, preferably, the pawl is resiliently biased against the formations on the rigid ratchet element.

Suitably, the pawl is in the form of a substantially flat spring an end of which bears against the formations on the rigid ratchet element.

Such a pawl is adapted to allow the ratchet element to slide with little resistance in one direction but to prevent any movement in the opposite direction.

In preferred embodiments, the formations are regularly spaced along the rigid ratchet element, and the pawl comprises a pair of pawl members resiliently biased against the rigid ratchet element at different points along the length of the rigid ratchet element, the axial distance between the pair of pawl members being different to the axial distance between successive formations.

The advantage of this arrangement is that by locating the ratcheting linkage between the pawl and the ratchet teeth, the teeth make alternating contact with either pawl member. The ratcheting member advances by increments which are less than the actual difference between successive formations on the ratchet.

In particularly preferred embodiments, the distance between successive formations is twice the distance between the pawl members. This means that then the ratchet advances in half steps and enables accurate delivery of even smaller incremental volumes of drug (if a full step is counted as equating to the distance between successive ratchet teeth formations.)

The definitions of "half steps" and "full steps" is not as arbitrary as it may appear, since one of the main constraints on the accuracy of delivery of small volumes, as explained above, is the manufacturing tolerances of the ratcheting teeth.

It is envisaged that one of the least expensive ratcheting mechanisms, and therefore one of the most suitable for large scale production, is a stamped plastics ratchet bar having a sawtooth surface, against which a pawl in the form of a leaf spring may be biased. The main limitation on accuracy in this system is likely to arise from the spacing of adjacent sawtooth formations which may not be able to be made accurately with the required spacing. In such cases the minimum delivery volume, all other things being equal, will be limited by this component. However, by employing a specially designed pawl or leaf spring (which can be made to much higher tolerances from metal materials at relatively low cost), accuracy is doubled, and the minimum deliverable volume may be halved.

In alternative embodiments, the ratchet teeth are regularly spaced along the rigid ratchet element, and the pawl comprises three or more members resiliently biased against the rigid ratchet element at regular intervals along its length. The axial distance between each successive pair of pawl members is chosen to be different to the axial distance between successive ratchet teeth.

Suitably, in such cases, the distance between successive ratchet teeth is given by the number of pawl members multiplied by the distance between each successive pair of pawl members.

Thus, by analogy with the two pawl members spaced at half of the distance between successive ratchet teeth, three or four pawl members would preferably be spaced at intervals of a third and a quarter, respectively, of the distance between successive ratchet teeth on the ratchet element.

Suitably, the pawl is in the form of a resilient member which terminates in a plurality of fingers biased against the ratchet element.

A preferred embodiment in this regard is a pawl which comprises a flat spring which is partly split to define fingers of different lengths.

In another preferred embodiment, the ratchet element comprises a helical spring and the pawl comprises one or more fingers which engage with the coils of the spring. The coils of a helical spring easily engage with the pawl fingers, and the regular spacing of the coils of a helical spring enable it to be used as a ratchet element.

A further advantage of this embodiment is that the size of the device can be minimised by taking advantage of the flexibility of the spring. Thus, whereas a rigid ratchet bar protruding from a drug cartridge before use might provide an unacceptably long device for certain applications (after use, the ratchet element might be partly or totally accommodated within the empty cartridge interior), a helical spring can be bent to be parallel with the cartridge to reduce the overall length.

Preferably, in embodiments which employ a helical spring in lieu of a ratchet element, one or more fixed fingers are mounted in fixed position relative to the housing, and one or more reciprocable fingers are mounted on the mechanism, such that when the one or more reciprocable fingers move in a first direction they engage the coils of the helical spring to drive the helical spring in the first direction, and when the one or more reciprocable fingers move in an opposite direction, the one or more fixed fingers engage with and hold the coils of the helical spring preventing it being driven back in the second direction, whereby the fixed and reciprocable fingers co-operate to drive the helical spring in one direction only.

The operation of this embodiment will become clearer from the description below. The fingers are generally arranged such that the helical spring is forced to alternately slip past the fixed fingers and the reciprocable fingers, which gives rise to a uni-directional driving movement. Suitably, each finger is inclined in the first direction. This makes it easier for the helical spring coils to slip past the fingers in this direction, and more difficult for the coils to push back in the opposite direction against the fingers.

Preferably, the position of the one or more fixed fingers relative to the one or more reciprocable fingers is such that the helical spring is driven by the reciprocable fingers towards the fixed fingers.

This feature helps prevent a situation which may develop in which a flexible helical spring is pulled by the reciprocable fingers away from the fixed fingers, but rather than slipping past the fixed fingers, the helical spring merely stretches, such that when the reciprocating fingers move back towards the fixed fingers the helical spring simply relaxes, without any net movement having taken place. The solution to this problem is achieved in part by pushing the helical spring towards the fixed fingers as the driving step of the delivery action.

Suitably, the minimum distance between the fixed and reciprocable fingers, respectively, is not greater than ten times the distance between adjacent coils of the helical spring when the helical spring is in a relaxed position. Preferably, this minimum distance between the fixed and reciprocable fingers, respectively, is not greater than five times the distance between adjacent coils of the helical spring when the helical spring is in a relaxed position, most preferably not greater than twice the distance between adjacent coils.

The reason for this again relates to the problem of using a flexible spring which is likely to stretch rather than be displaced. While the problem could be overcome by using a sufficiently stiff spring, this would defeat the purpose of using this type of spring, which is to allow the ratchet element to be bent within the housing to reduce overall dimensions. While even a stiff spring can be bent under sufficient force, this tends to generate frictional forces which would prevent the spring from sliding past the ratchet fingers.

Instead, setting the two sets of fingers close together allows even a relatively very flexible spring to be used without much stretching, since for a given overall amount of stretching, a greater stiffness is achieved by concentrating this stretching over just a few coils.

Thus, in certain preferred embodiments, the minimum distance between the fixed and reciprocable fingers, respectively, is approximately equal to the distance between adjacent coils of the helical spring when the helical spring is in a relaxed position.

Suitably, the mechanism comprises a flexible ratchet element which is sufficiently stiff to drive medicament from the chamber when driven by the member, and sufficiently flexible to be bent before it meets the member, whereby the overall length of the device is reduced relative to a device in which a rigid ratchet element protrudes linearly from the mechanism before use. Thus, the flexible member may be, for example, a piece of bendable thermoplastics stamped or molded with a ratchet sawtooth profile.

In order for this embodiment to be useful, the flexible member should have a degree of flexibility which allows it to be bent sufficiently to reduce the overall dimensions of the device. Furthermore, it must nevertheless be sufficiently stiff to transmit the driving force of the ratcheting mechanism without buckling or distorting to any great extent. This can be achieved by restraining the degree of freedom of movement of the member.

For example, by driving a flexible member into a conduit in which the flexible member makes a good fit, the flexible member is prevented by the conduit walls from bowing or buckling sideways. Thus, when driven by the ratchet mechanism the flexible member is constrained to transmit the driving force to the piston, and despite its flexibility it acts as a drivable piston rod. Other mechanisms not requiring a restraining conduit are also possible, as described below.

Preferably, the mechanism comprises two or more co-operating flexible ratchet elements which are individually sufficiently flexible to be bent before they meet the member but when joined together are together sufficiently stiff to drive medicament from the chamber when driven by the member.

Further, in a preferable embodiment, the two or more co-operating flexible ratchet elements are bent away from one another before they meet the member.

Suitably, the device according to the invention further comprises electronic control means for controlling the delivery rate. Preferably, the electronic control means comprises a timing mechanism which alternately energises and de-energises the gas generating mechanism for controlled periods.

As explained above, by choosing an energized period long enough to always guarantee complete advancement of the ratchet mechanism by a predetermined number of steps, and by providing a de-energised period (e.g. for venting) which allows relaxation of the system, the amount of drug delivered in this overall cycle is accurately controllable independently of variations (within reason) in the gas generation rate.

Furthermore, the use of a timer allows the overall cycle length to be varied in a controlled manner over time, thereby providing an accurately controllable device which delivers at a time-varying rate. Such devices find a particular application in the field of chronotherapeutics.

Further, preferably, the electronic control means is programmable for different delivery programs. The control means may be user-programmable or a single unit may be factory-programmable for different delivery regimes (e.g. for different drugs. Preferably, the device according to the invention further comprises means for manually adjusting the delivery rate. This allows for a certain degree of flexibility which might be desirable where the user can safely have an amount of control over the treatment. Alternatively, it can be set by the physician or pharmacist and disabled to prevent patient interference.

In preferred embodiments, the member reciprocates to cause the incremental advancement of the mechanism and the means for manually adjusting the delivery rate comprises means for limiting the travel of the member, whereby the volume of drug delivered on each reciprocating stroke is controllable. Thus, a simple advancing screw can control a stop against which any reciprocating element ends its travel. If this is used, adjustment of the screw will provide a control mechanism. For example, a device could be designed with three delivery rates, namely low, medium and high, corresponding respectively to one, two and three ratchet advancements per reciprocation. A simple mechanism would determine how far the reciprocating mechanism is allowed to advance on each stroke, to determine the delivery rate. Clearly, more sophisticated embodiments could also be achieved. Devices having the ability to deliver bolus doses of drug are preferred in therapies such as patient controlled analgesia.

In a preferred embodiment, the means for manually adjusting the delivery rate provides the user with the ability to deliver a bolus dose of drug. It is advantageous if the bolus dose can be delivered without this interfering with the normal basal delivery rate.

When the reciprocating mechanism comprises a lever arrangement, it is preferred that the means for manually advancing the mechanism comprises means for manually advancing the lever extending between the chamber and the mechanism, operable from the exterior of the housing. Any suitable mechanism, such as a knob, button or lever can be used to operate the lever.

Preferably, the mechanism comprises a ratchet and wherein the means for manually advancing the mechanism comprises a pawl which is manually reciprocable from the exterior of the housing.

Further, preferably, the mechanism for manually advancing said lever is provided with gradations corresponding to a number of stepwise advances of the ratchet mechanism.

For example, in delivering insulin, the advancing means could be marked in units which would be understood by the patient, and the scale would be calibrated to correspond to the delivery of the correct dose.

In a further aspect, the present invention provides a method of delivering drug to a patient. The method includes affixing a drug delivery device to the surface of the patient's skin. The drug delivery device having a housing containing a drug reservoir, means for facilitating expulsion of drug from the drug reservoir, a mechanism in communication with the facilitation means, operable to undergo incremental advancement and thereby drive the drug from the reservoir, a member operatively associated with the mechanism to cause the incremental advancement of the mechanism as the member moves in a first direction, and a gas generator located within the housing and operable to expand in a chamber, the member being in transmission relation to the chamber. The method further includes activating the device whereby the member is driven by the movement of the chamber to advance the mechanism and thereby drive the drug from the reservoir in incremental fashion.

Other objects, features and advantages of the present invention will become apparent upon reading the following detailed description, when taken in conjunction with the drawings and appended claims.

BRIEF DESCRIPTION OF THE DRAWINGS

The invention will be now be described with reference to the accompanying drawings, which illustrate the preferred embodiments of the present invention and in which:

FIGS. 7-11 are sectional side views of a second embodiment of a device according to the invention, shown at successive points during its use;

FIG. 23 is a sectional plan view of the embodiment of FIG. 22 when ready for use;

DETAILED DESCRIPTION OF THE PREFERRED EMBODIMENTS

Figure 1:
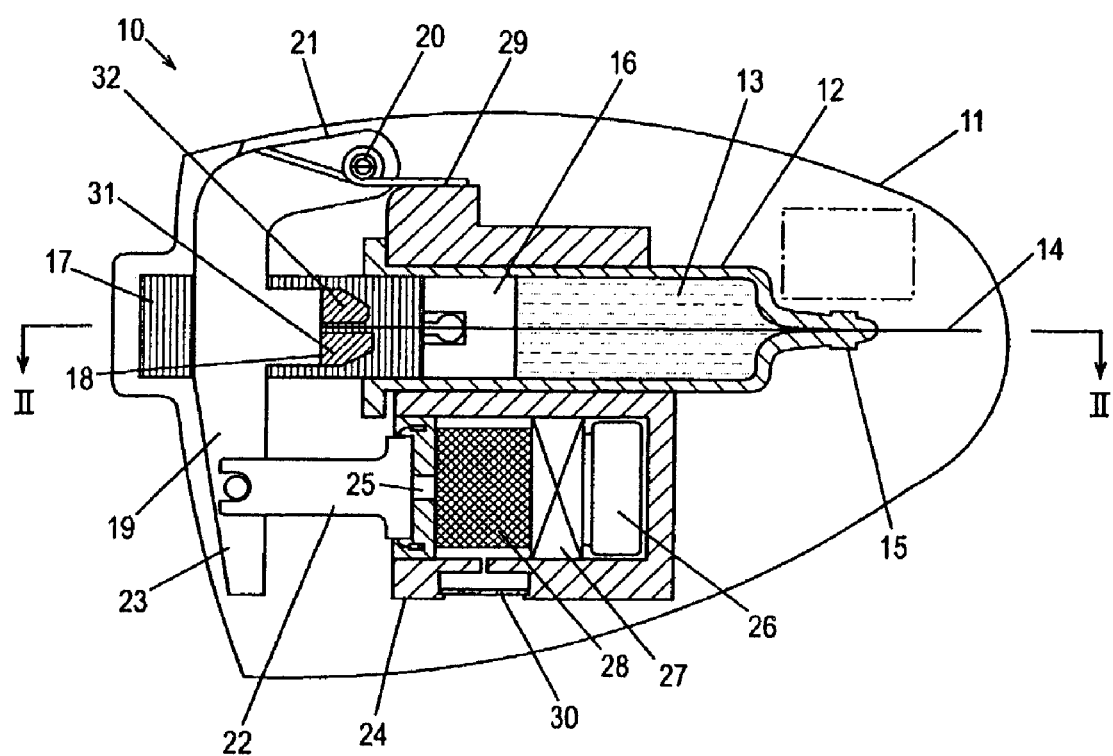
FIG. 1 is a sectional plan view of a first embodiment of a drug delivery device according to the invention.

Referring now in more detail to the drawings, in which like numerals indicate like parts throughout the several views, in FIG. 1 there is indicated, generally at 10, a drug delivery device according to the invention. The device 10 comprises a housing 11 containing a cartridge 12 filled with a drug 13. The cartridge 12 is provided with a needle 14 extending from a first end 15 of the cartridge for delivery of drug 13 to a patient. A piston 16 is slidably received in the cartridge 12, such that when the piston 16 is pushed towards the first end 15, drug is forced from the cartridge 12 out through the needle 14.

The piston 16 is mounted on a ratchet bar 17 which is driven by a pawl 18 mounted on a reciprocable lever 19. Lever 19 is mounted on an axis 20 at one side 21 and is connected to a driving rod 22 at the other side 23, whereby reciprocation of the driving rod 22 causes pawl 18 to reciprocate with respect to the ratchet bar 17. As will be explained in greater detail below, this causes the ratchet bar 17 to advance stepwise towards the first end 15 of cartridge 12 and thereby drive the drug 13 from the cartridge.

The driving rod 22 is in connection with a flexible diaphragm 24 which defines a wall of a gas generation chamber 25. A battery 26 is connected via a microprocessor 27 to an electrolytic cell 28 which is operable to generate a gas into chamber 25. When gas is generated, the chamber expands and causes the diaphragm 24 to move. This movement pushes the driving rod 22 in the direction away from the first end 15 of cartridge 12. The movement is opposed by a return spring 29 which biases the lever 19 towards the first end 15. After a certain period of time the chamber 25 is fully expanded and the supply of current from the battery 26 to the electrolytic cell 28 is switched off by the microprocessor 27.

A silicone membrane 30 defines a wall of the chamber 25. The membrane 30 is slightly permeable and thus allows a controlled leakage of gas from the chamber 25. When the chamber 25 is in its expanded state, the force of return spring 29 will act to decompress the chamber 25 by gas leaking through membrane 30. After the chamber 25 has fully decompressed in this manner, the lever 19 and hence the pawl 18 will have made one complete reciprocation thereby advancing the ratchet bar 17 by a fixed step.

For example, the cycle might be chosen to allow the delivery of a quantity of drug corresponding to the advancement of a single step of the ratchet bar 17 every five minutes. In such a case the electrolytic cell 28 could be switched on for one minute and then switched off for four minutes. As long as the timing of the microprocessor is accurate, this will ensure that precisely one stepwise advance is made in that five minute period.

The precision of device 10 is to a certain extent independent of the exact quantity of gas generated because the ratchet bar 17 is quantised, i.e. it can only move by a fixed step (or number of steps) at a time. Similarly, because the membrane 30 provides a controlled constant leakage from the system even during gas generation, other minor leaks which might affect the accuracy of conventional gas driven delivery devices are not important (although of course if the leak is bad enough the chamber will be unable to pressurise fully when the gas is generating).

It will be noted from the first embodiment shown in FIG. 1 that pawl 18 is split in two halves, i.e. a longer half 31, and a shorter half 32. The pawl 18 is a leaf spring which is biased down onto ratchet bar 17. The halves 31,32 of the pawl 18 are of unequal length.

Figure 2:
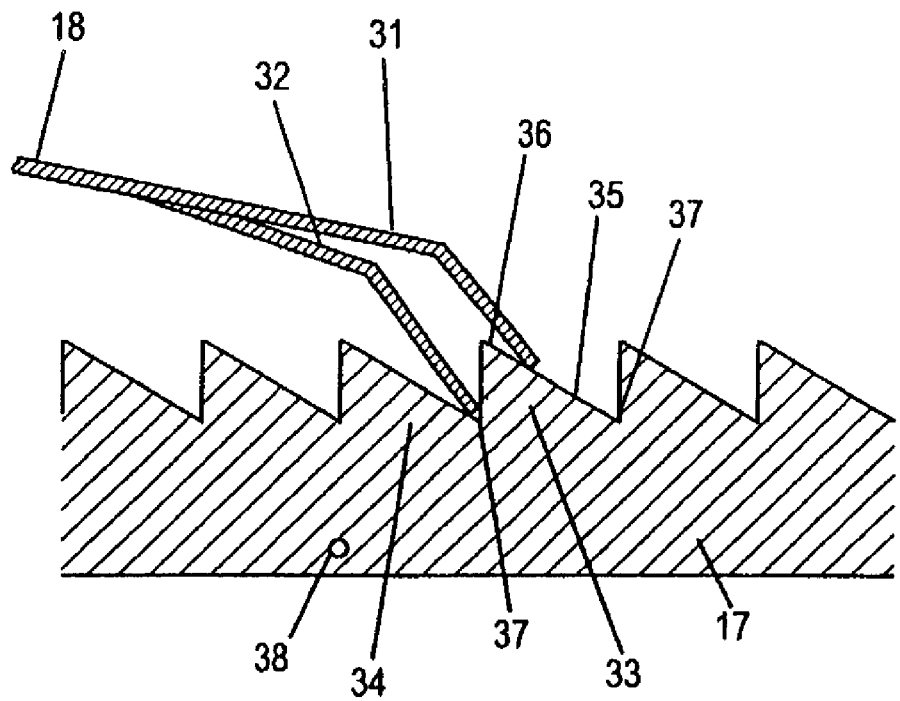
FIGS. 2-5 are schematic views of a detail of the embodiment of FIG. 1 shown at successive points in the operating cycle.
Figure 2A:
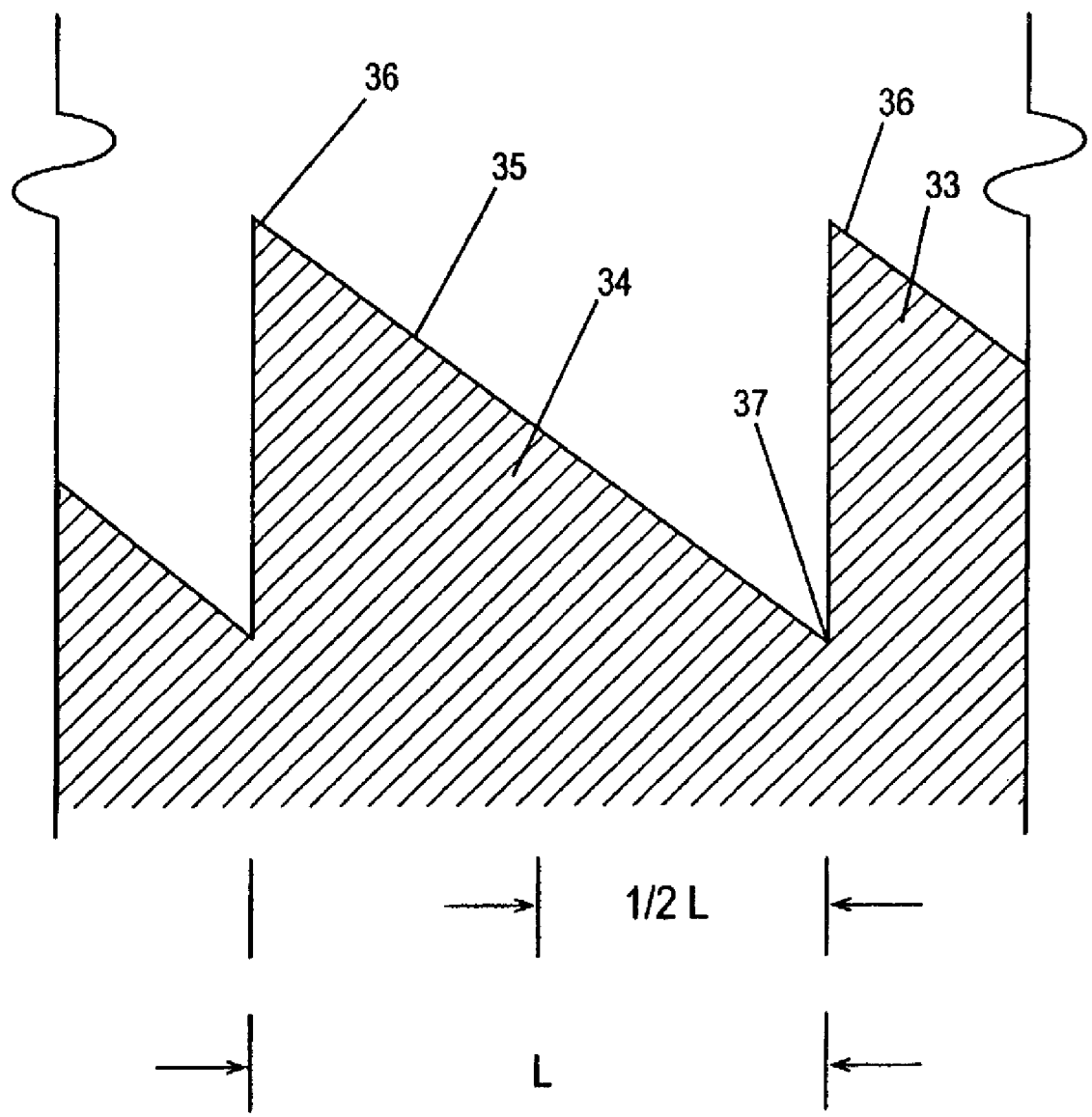

FIG. 2 shows a cross-sectional enlarged view of a portion of the ratchet bar 17 which has a series of evenly spaced steps or teeth 33,34. The difference in length between the halves 31,32 of the pawl 18 is exactly half of the distance between adjacent teeth 33,34 on the ratchet bar 17. It can be seen that each tooth 33,34 has a sloped surface 35 having a peak 36 and a trough 37, as shown in detail in FIG. 2A. At the point of the cycle illustrated in FIG. 2, the longer half 31 of the pawl 18 presses against the sloped surface 35 of tooth 33, midway between the peak 36 and trough 37, and the shorter half 32 presses against the trough 37 of the adjacent tooth 34.

When gas is generated to drive the driving rod 22 in the direction away from the first end 15 of cartridge 12 (see FIG. 1), the two halves 31,32 of the pawl extending from lever 19 (FIG. 1) move left as viewed in FIG. 2. This results in the situation shown in FIG. 3, in which the shorter half 32 has been pushed back up the sloped surface 35 of tooth 34, and the longer half 31 has passed the peak 36 of tooth 33 to rest in the trough 37 of adjacent tooth 34 formerly occupied by the shorter pawl half 32. In practice, the distance travelled by the pawl 18 will be slightly further than the minimum necessary so as to allow for any variations between components. This does not affect the operation of the invention as a whole since the pawl 18 when making its return stroke will press against the correct tooth as it begins its travel.

Figure 3:
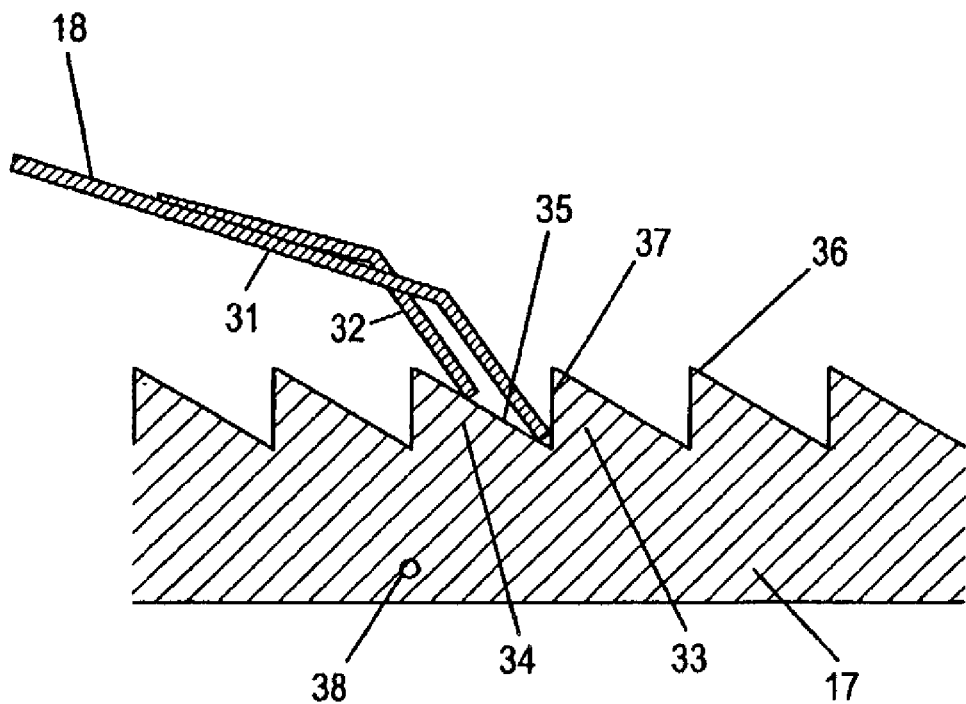
Figure 4:
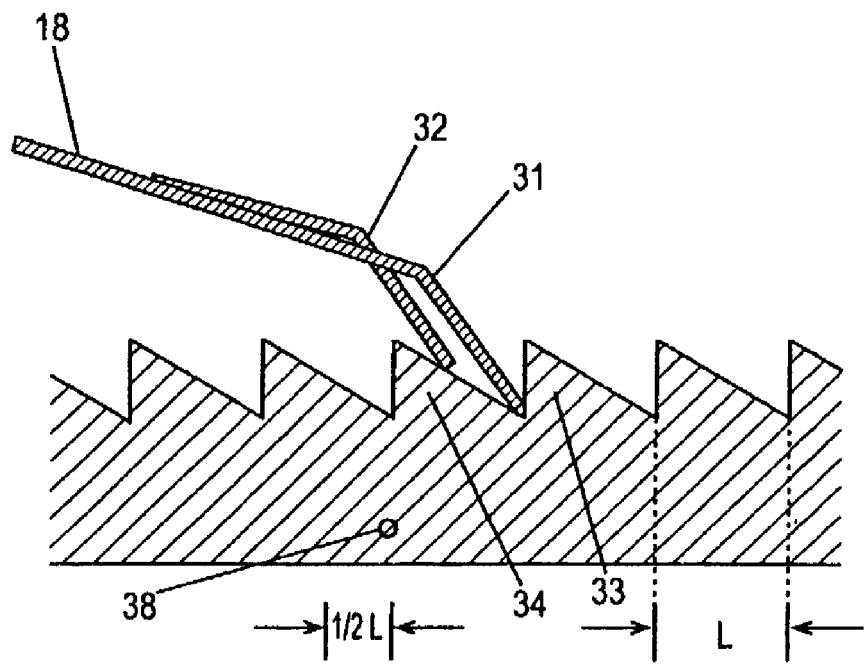

After the gas generation chamber 25 is pressurised fully and the device 10 is in the FIG. 3 position, gas generation ceases and the controlled leakage from the chamber 25 allows the return spring 29 to push the lever 19 back to its starting position, leading to the configuration shown in FIG. 4.

Figure 5:
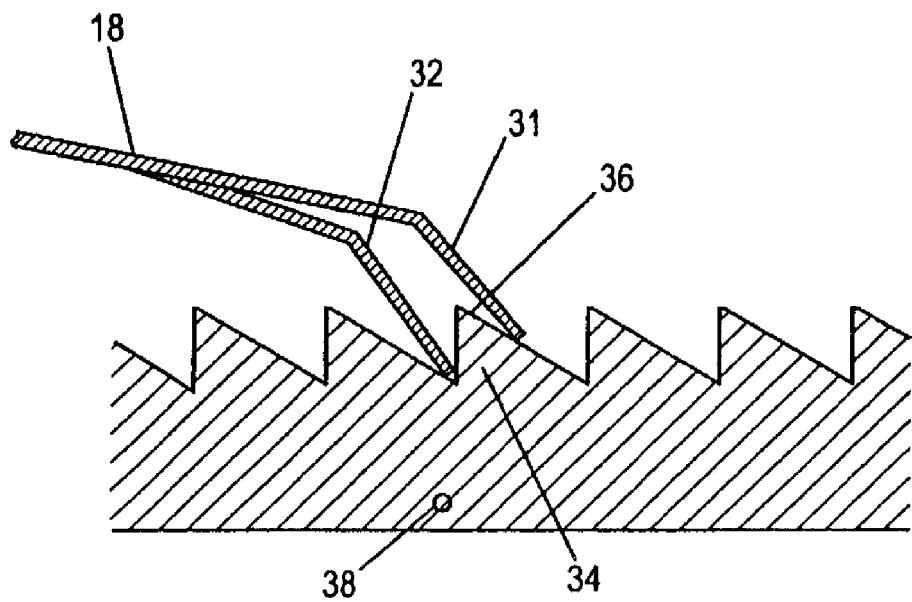

In FIG. 4, the longer pawl half 31 when being driven forward (i.e. to the right) has abutted against tooth 33 and pushed the ratchet bar 17 forward. This completes one reciprocation of the pawl 18, and when the electrolytic cell 26 again fills the gas generation chamber 25 to drive the pawl 18 to the left (as seen in FIG. 5), the short pawl half 32 passes over the peak 36 of tooth 34 as shown in FIG. 5, ready to push against tooth 34 and thereby once again advance the ratchet bar 17.

The reason for using a pawl in two halves of unequal length is seen by observing the movement of a point 38 on the ratchet bar. After a complete cycle has been completed, i.e. from FIG. 2 to FIG. 5, the point 38 has moved by a distance ½ L. This is exactly half of the length L of one of the teeth 33,34 on the ratchet bar 17, as can be seen with reference to FIG. 2A.

In effect this means that although the manufacturing quality and tolerances are such that the tooth length is not as small as what would be desired (perhaps because the manufacturing technique, chosen for its cost effectiveness, is incapable of achieving a smaller length of adjacent teeth), it is nevertheless possible to deliver amounts of drug corresponding to an advance of half of the length of one of the teeth 33,34, thereby halving the minimum deliverable volume.

Figure 6:
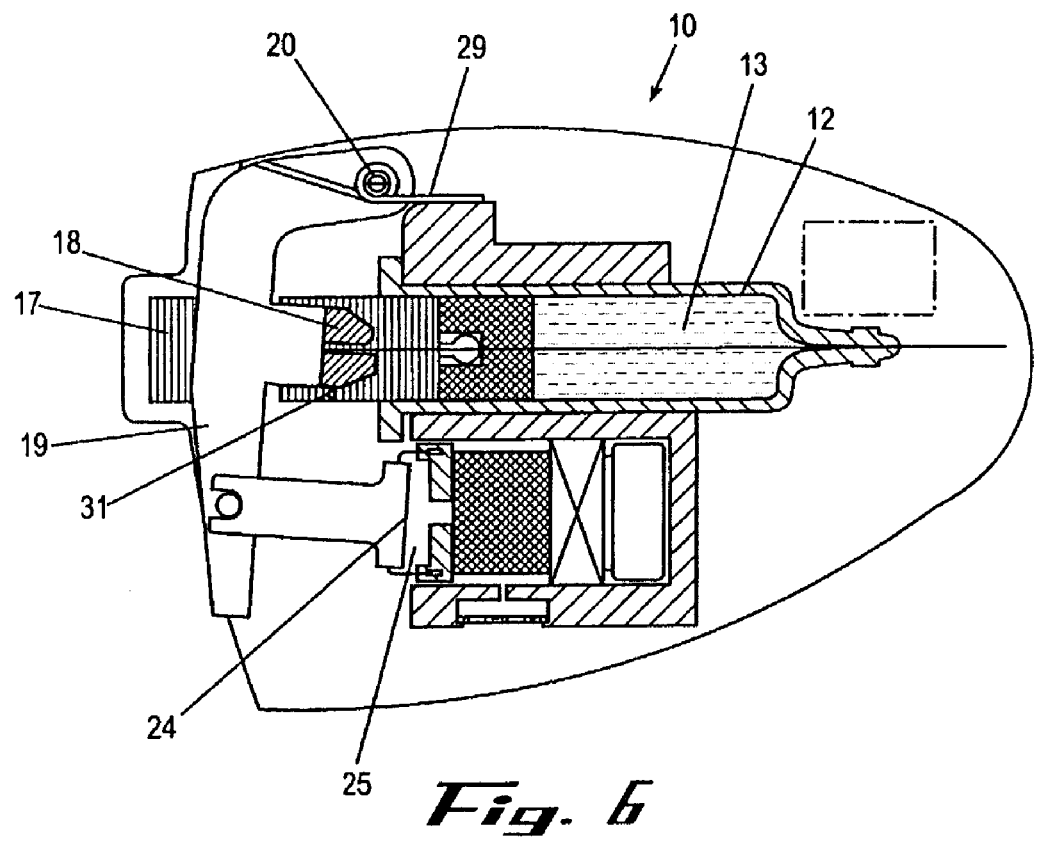
FIG. 6 is a sectional plan view of the embodiment of FIG. 1, in use.

FIG. 6 shows the device of FIG. 1 in operation at the completion of gas generation, and before the lever 19 has begun its return stroke. Thus, it can be seen that gas generation chamber 25 has expanded by pushing the diaphragm 24 outwards, and the lever 19 is thus pivoted on its axis 20 against the force of the return spring 29. When the lever 19 is driven back to the FIG. 1 position, a small volume of liquid drug 13 will be forced from the cartridge 12.

Because the device of FIG. 1 delivers small volumes in a stepwise fashion, it is possible to achieve an extremely low delivery rate. For example instead of operating in 5-minute cycles, the gas generator 25 could be activated for 1 minute as previously described and then switched off for 59 minutes to give cycles of one hour duration. Unlike other gas-driven devices which cannot achieve these long-term low-volume rates because of pressure losses in the system, the device 10 of the present invention does not require a system pressure to be maintained above atmospheric pressure.

As can be seen from FIGS. 1 and 6, the volume of the gas generation chamber 25 is small relative to the size of the device. This minimises variations in the volume of gas per stroke, and helps ensure a constant delivery rate. Preferably, the device 10 will generate in excess of 10-30% volume of gas over the required amount on each stroke so that the device can compensate of variations due to temperature, atmospheric pressure, materials used, etc. (The device will never drive the ratchet 10-30% further than necessary, since the ratchet can only move in fixed steps.) This extra gas is stored as an overpressure in the system and is of course released during the venting part of the cycle.

Figure 7:
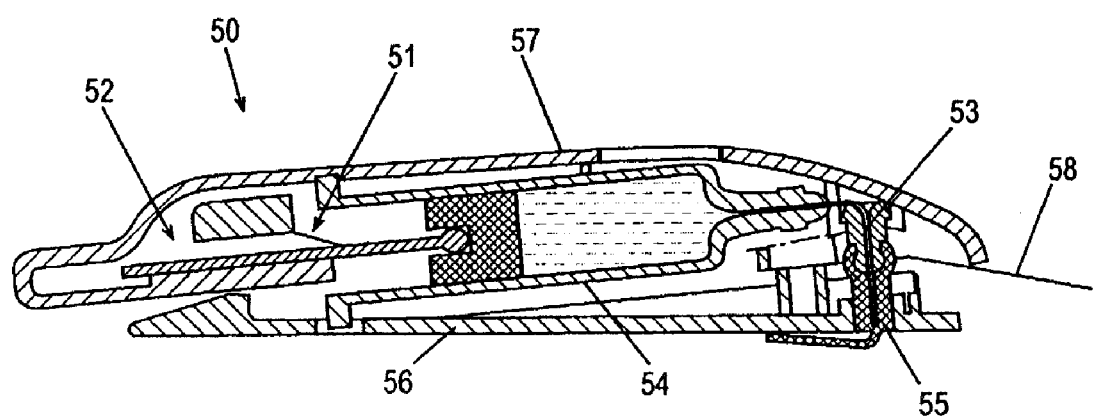

FIG. 7 shows a cross-sectional side view of a second alternative embodiment of the present invention, indicated generally at 50. The device 50 is similar in most respects to the first embodiment shown in FIG. 1. In the device of FIG. 7, however, the pawl 51 is not split into two halves, so that it advances the ratchet bar 52 by full steps equal to the tooth length ("L"). In all other respects the device 50 is identical to the device 10 of FIG. 1. It can be seen from FIG. 7 that the needle 53 of the device 50 (as with the FIG. 1 device) is bent at 90° to the axis of the cartridge 54.

The device 50 of FIG. 7 is shown before use. A protective sheath 55 is provided on the needle 53 and a displaceable lower cover 56 is hinged to the main housing 57 by a hinge (not shown). The displaceable lower cover 56 and the main housing 57 are prevented from moving relative to one another by a safety tab 58. The lower surface 61 of the displaceable cover 56 is covered by a contact adhesive which is protected before application to the user by a protective liner 60. The liner 60 has a pull tab 59 to ease removal of the liner by the user immediately before application of the device 50.

Before use, the protective sheath 55 is removed as indicated in FIG. 8 by grasping and pulling the pull tab 59. This also causes the release liner 60 to be pulled away revealing the contact adhesive on the lower surface 61 of the displaceable cover 56. The lower surface 61 is adhered to the user's skin. Then, the safety tab 58 is pulled away from the device 50 as shown in FIG. 9.

Figure 10:
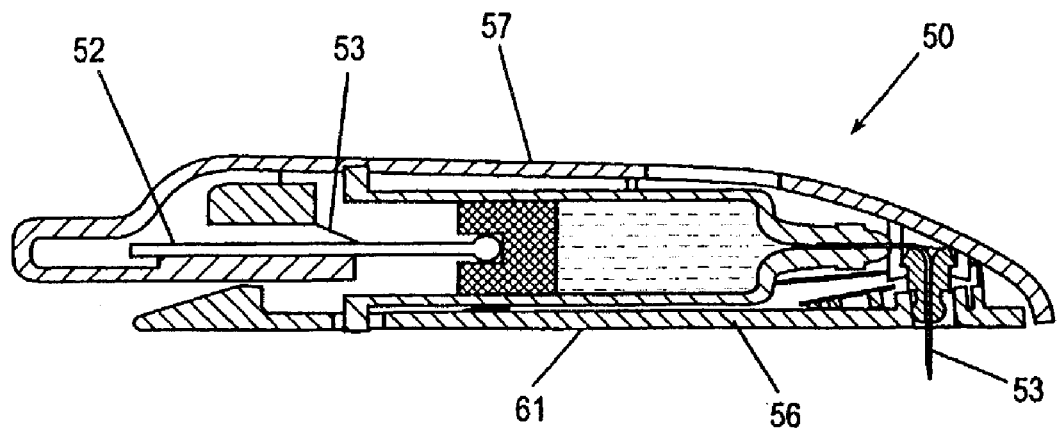

As shown in FIG. 10, the main housing 57 is then pressed towards the skin whereupon it snaps towards the displaceable cover 56. The needle 53 projects beyond the lower surface 61 to penetrate into the skin for subcutaneous drug delivery.

The delivery mechanism is then actuated, either by the user, or more preferably, in automatic fashion by the microprocessor. Upon activation either manually or automatically, the ratchet bar 52 is advanced by the pawl 53 in stepwise manner as described above with regard to the operation of the first embodiment as shown in FIG. 1.

Figure 11:
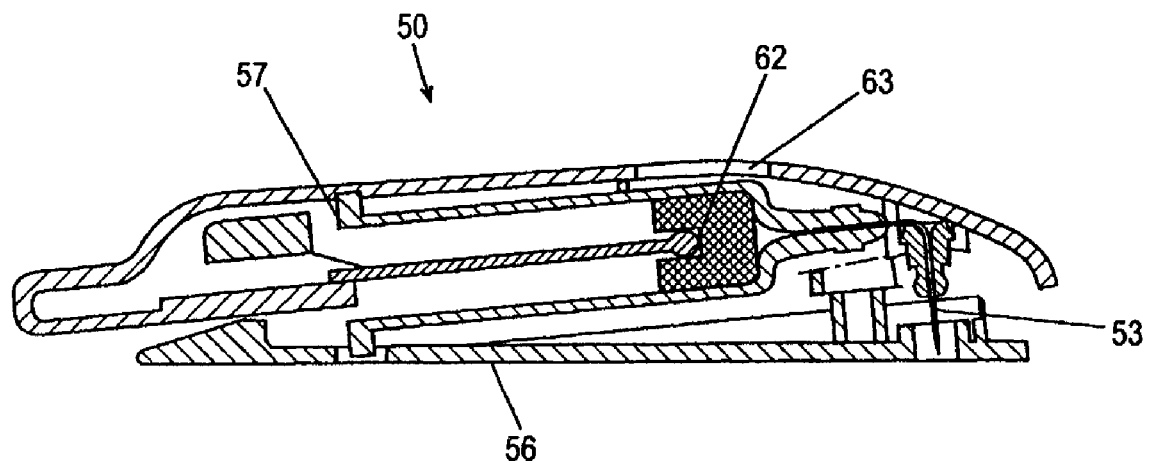

When delivery is completed (see FIG. 11) the user can see the piston 62 through an aperture 63 in the main housing 57 as shown in FIG. 11. The main housing 57 is then pulled away from the skin whereupon it snaps away from the displaceable cover 56 and locks in this position by a locking mechanism (described in more detail in our U.S. Provisional Application No. 60/045,745) which prevents further actuation of the device, i.e. prevents the needle 53 from projecting beyond the displaceable cover 56 due to further relative movement of the main housing 57 and the displaceable cover 56.

Figure 12:
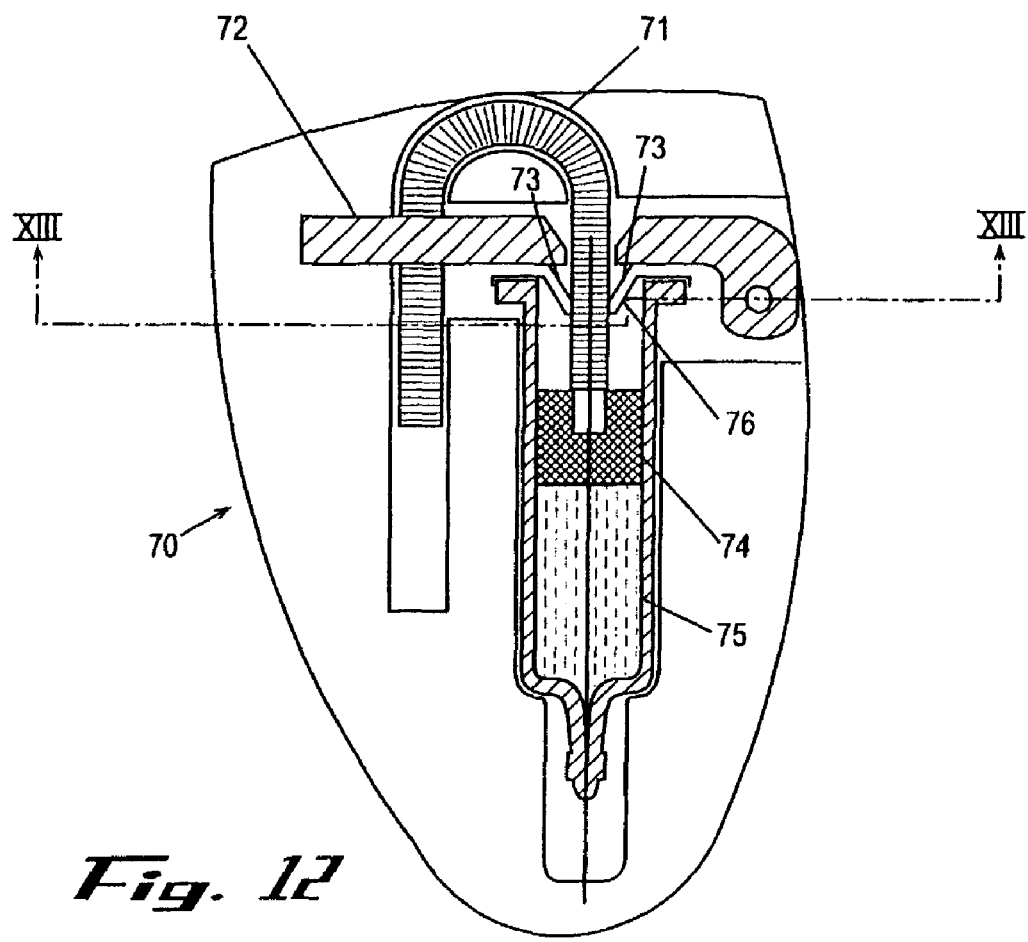
FIG. 12 is a simplified sectional plan view of a third embodiment of a drug delivery device according to the invention.

In FIG. 12 there is indicated, generally at 70, a further embodiment of a device according to the invention. In the illustration of this embodiment, only those details necessary to understand the differences relative to the devices of the first and second embodiments are shown, and thus the gas generation mechanism, for example is not shown.

In the device of FIG. 12, the ratchet bar has been replaced by a helical spring 71. A lever 72 is caused to reciprocate in identical manner to that previously described. A pair of resilient reciprocable fingers 73 are mounted on the lever 72 and reciprocate as the lever reciprocates. These reciprocable fingers 73 are inclined in the direction of movement of the piston 74 as it empties the cartridge 75. Thus, when they move in the direction in which they are inclined they tend to grip and push the coils of the helical spring 71 forward. As the helical spring 71 moves forward it slips past a pair of resilient fixed fingers 76 mounted directly in front of the reciprocable fingers 73, and inclined in identical manner.

When the lever 72 moves away from the piston 74 (as the gas generator generates the gas) the helical spring 71 is prevented from moving back because it is gripped by the fixed fingers 76. The reciprocable fingers 73 thus slip over the coils of the helical spring 71. When the lever 72 reverses its travel again the helical spring 71 is again gripped and pushed forward by the reciprocable fingers 73.

Figure 13:
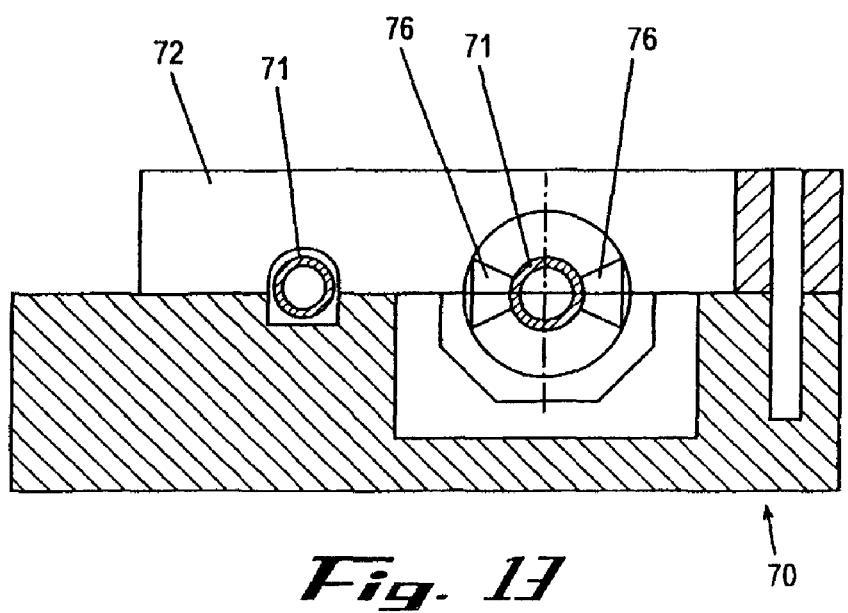
FIG. 13 is a cross sectional side view of the embodiment of FIG. 12, taken along the line XIII-XIII.

FIG. 13 shows a sectional side view of the device taken along the line XIII-XIII (in FIG. 12), in which the fixed fingers 76 and helical spring 71 are visible.

Thus, the arrangement of reciprocable fingers 73 and fixed fingers 76 act as a pawl and the helical spring 71 acts as a ratchet, such that on each reciprocation of the lever 72, the helical spring 71 advances by an amount equal to a set number of coil diameters. Accordingly, as with previously described embodiments, precisely controlled delivery rates are achievable, and in particular, extremely low volume delivery rates are possible with this invention.

While there is a tendency for the helical spring 71 simply to stretch between the reciprocable fingers 73 and the fixed fingers 76, this tendency can be overcome by choosing the correct stiffness (for both sets of fingers). Furthermore, the closer together the reciprocable fingers 73 and fingers 74 are mounted, the less likely the helical spring 71 is to stretch, since the force is spread over fewer coils.

One advantage of this embodiment is that because the helical spring 71 is curved within the device 70, it does not have to project directly out of the cartridge 75 and thus a shorter device can be realised, or the shape of the device can be varied as required.

Figure 14:
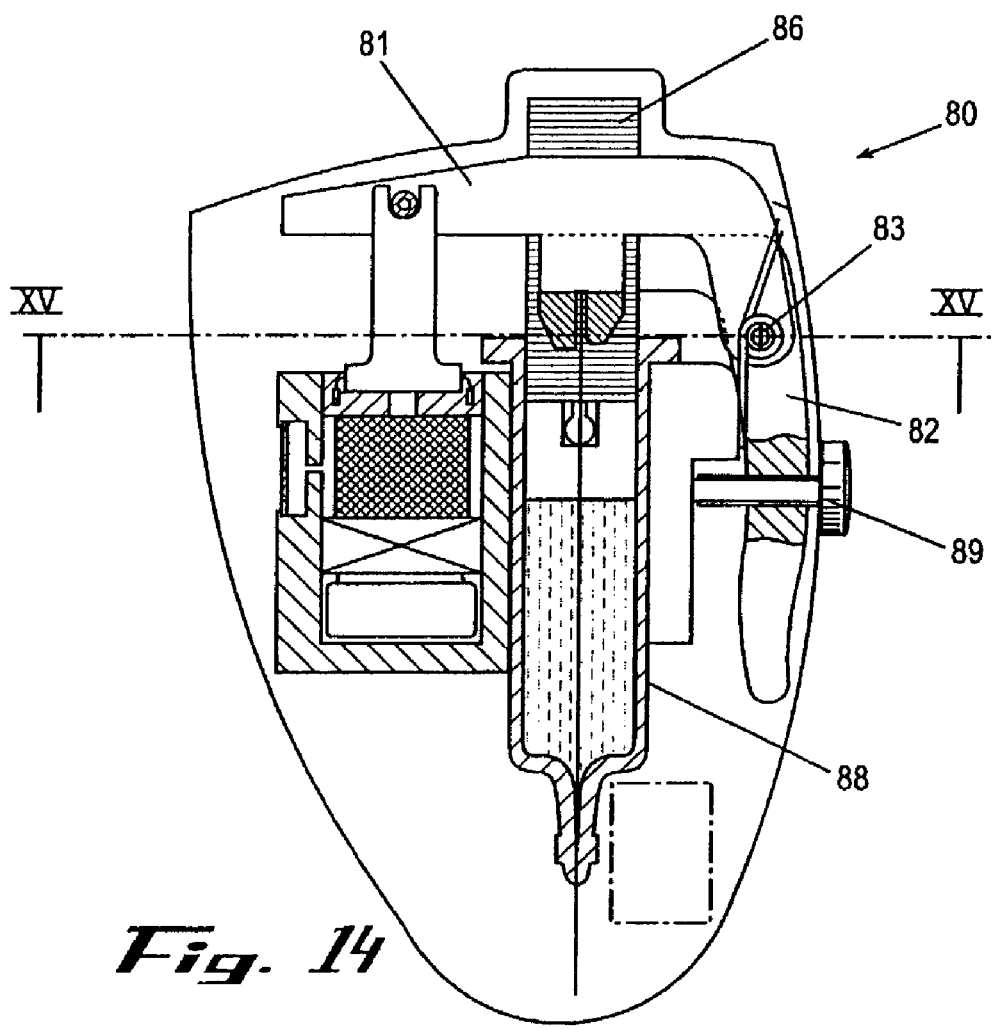
FIG. 14 is a sectional plan view of a fourth embodiment of a drug delivery device according to the invention.
Figure 15:
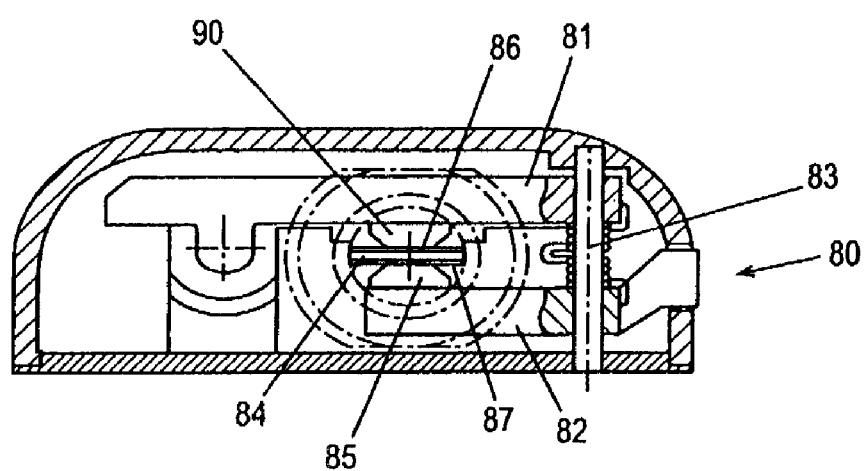
FIG. 15 is a cross sectional side view of the embodiment of FIG. 12, taken along the line XV-XV.

A further embodiment of the present invention is shown in cross-sectional plan view in FIG. 14. The device, indicated generally at 80, is in many respects identical to the device of FIG. 1 but differs in that as well as the gas-driven lever 81, a second manual lever 82 is provided. Manual lever 82 is mounted on a common axis 83 with gas-driven lever 81, as can be seen referring additionally to FIG. 15. Manual lever 82 passes under the ratchet bar 84 and also carries a second pawl 85. Both the upper surface 86 and lower surface 87 of ratchet bar 84 are provided with ratchet teeth, so that either gas-driven lever 81 or manual lever 82 can drive the ratchet bar 84 forward.

Thus, in normal operation, gas-driven lever 81 will drive the drug from the cartridge 88, and in this mode, the ratchet bar 84 simply slides past the pawl member 85 on manual lever 82 as described previously. However, if a bolus dosage of drug is required at any point in time, the manual lever 82 can be actuated to advance the ratchet bar 84 by a pre-determined number of teeth. Referring to FIG. 14, the manual lever 82 can be seen to have an adjustable threaded locking member 89 which determines the extent of travel of the manual lever 82, and hence the volume of the bolus delivery. In FIG. 14, the lever 82 is prevented from travelling because the threaded member 89 is fully torqued, and this locks the lever 82 preventing it from being actuated. However, if the threaded member 89 is partially torqued and thereby partially withdrawn from the housing in the axial direction, the lever 82 is free to move inwards by an amount equal to the distance of axial travel of the threaded member 89. The lever 82 can then be actuated by depressing the threaded member 89. The degree of travel of the lever 82 is determined by the extent to which the threaded member 89 is turned, and by providing marked gradations on the threaded member 89 one can give the user visual control over the volume delivered in such a bolus dosage.

The movement of the ratchet bar 84 under the action of the second pawl 85 is independent of the primary pawl- and ratchet mechanism. Thus, the second pawl 85 will, when actuated manually, advance the ratchet bar 84 by a whole number of steps. When advanced in this way, the ratchet bar 84 slides under the pawl member 90 on gas-driven lever 81, but this has no effect on the basal delivery rate or on the operation of the gas-driven delivery mechanism 80. Thus, each individual ratchet mechanism is independent of the other, and bolus delivery can take place against the background basal rate without complication.

Figure 16:
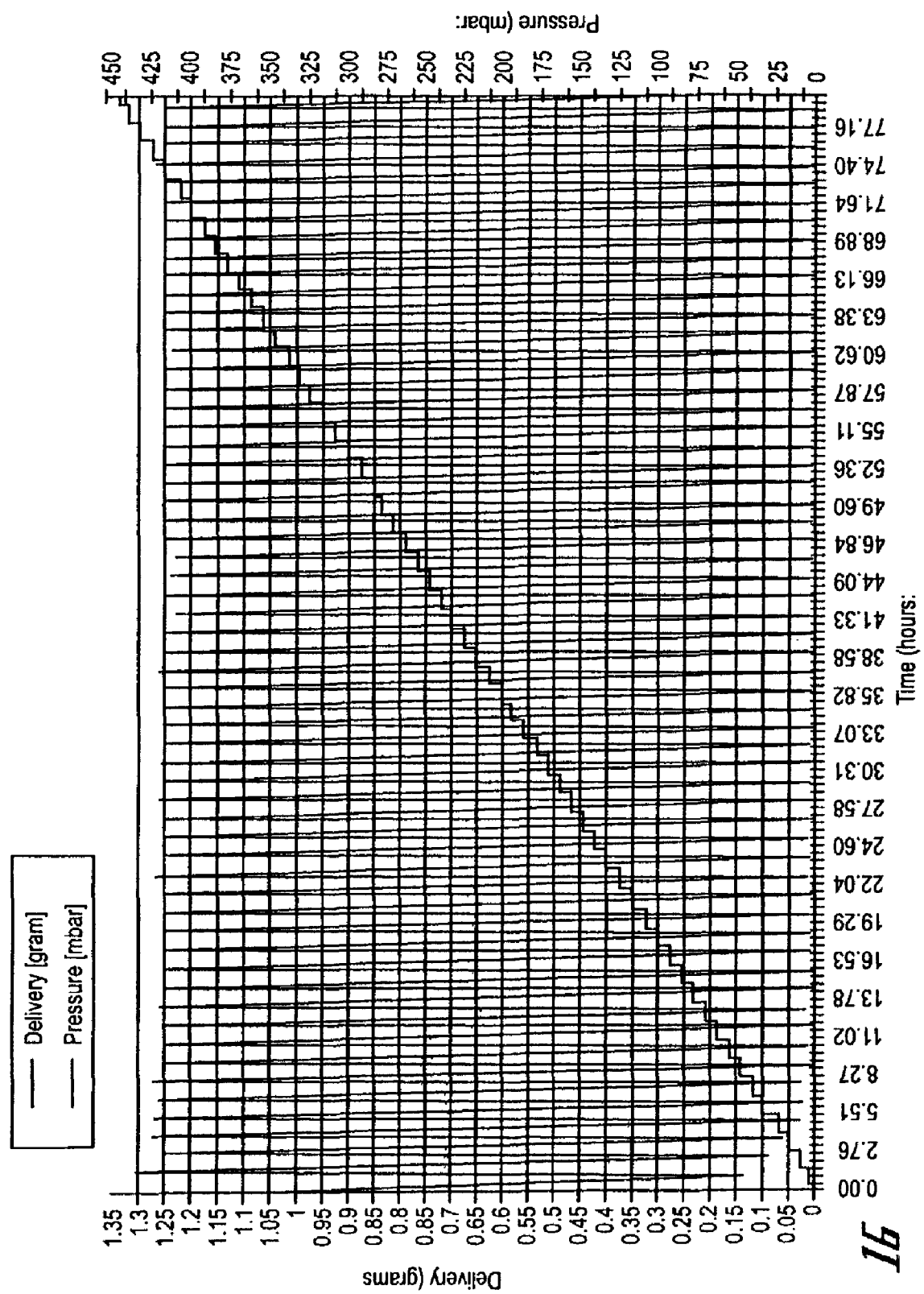
FIG. 16 is a graph showing the test results of an 80 hour test which plots delivery pressure and amount of drug delivered against time.

FIG. 16 is a graph of typical results achieved in a test of a device according to the invention, of the design shown in FIG. 1. The graph shows two lines, namely the cumulative delivery of drug against time (the stepwise steadily ascending line), and the delivery pressure against time (the line consisting of a succession of sharp peaks and troughs).

It can be seen that the device was tested over an 80 hour period (more than 3 days) and delivered just under 1.35 grams of drug solution in this time. This gives a delivery rate of less than 17 μg/hour. Furthermore, this delivery rate is absolutely constant, i.e. shows no deviation from a straight line. Accordingly, the device of FIG. 1 has a delivery rate whose accuracy is unmatched in the prior art, particularly for extremely slow delivery rates.

Figure 17:
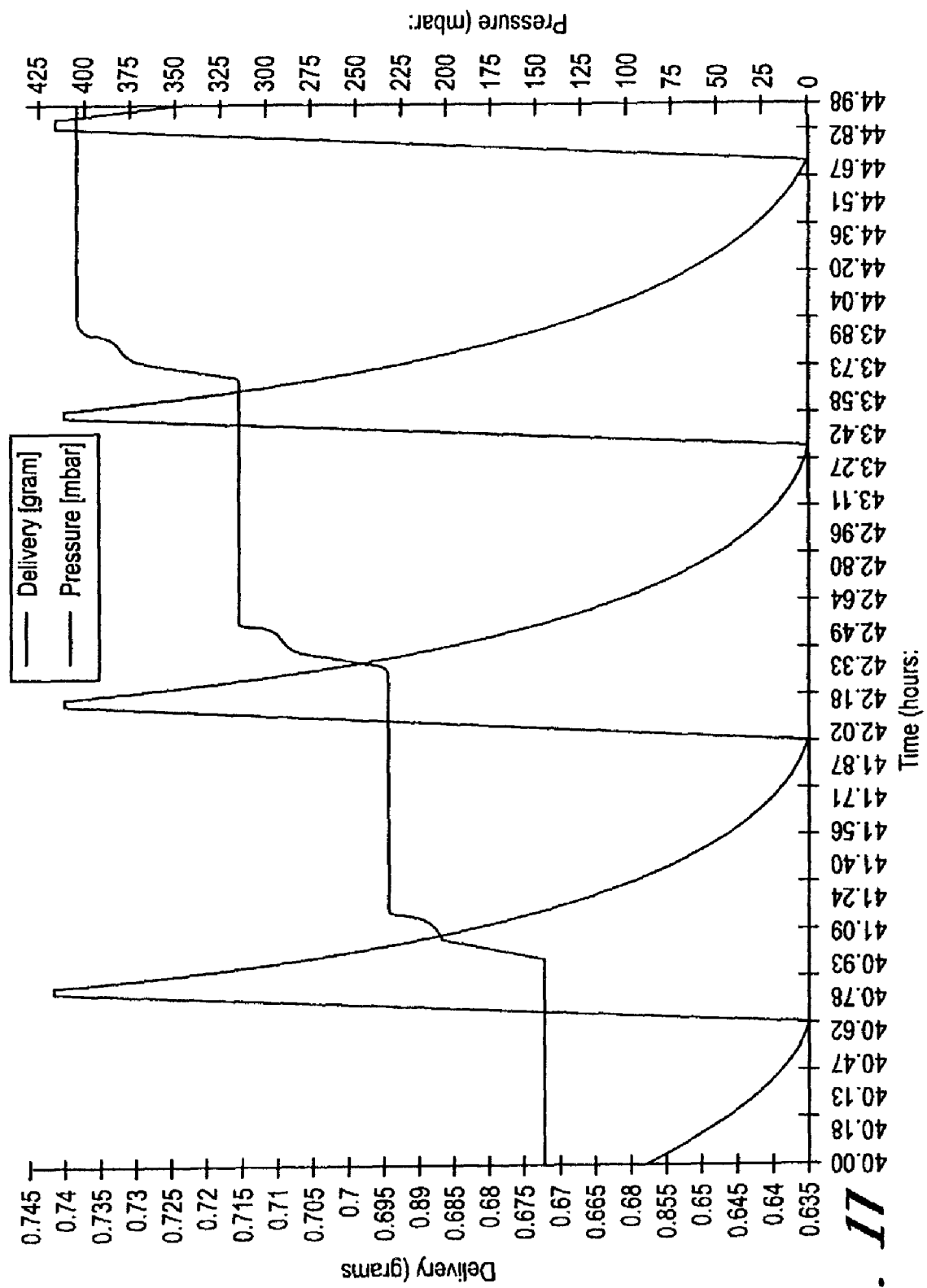
FIG. 17 is an enlarged detail of a portion of the graph of FIG. 16.

FIG. 17 shows a portion of the graph of FIG. 16 in greater detail, over a five hour period in the middle of the test. It can be seen that the pressure on each cycle immediately shoots up to a maximum, and then slowly falls off as gas is released through the silicone membrane.

It can be seen that the delivery overpressure reaches over 400 mbar (0.4 atm or 40 kPa) on each cycle, and this assists in providing a constant delivery rate, since any minor needle blockages will be forced out, and variations in blood pressure (when intravenous delivery is effected will have a negligible effect on the delivery rate. This is to be contrasted with other low volume pumps which generally achieve low delivery rates with low delivery pressures.

Figure 18:
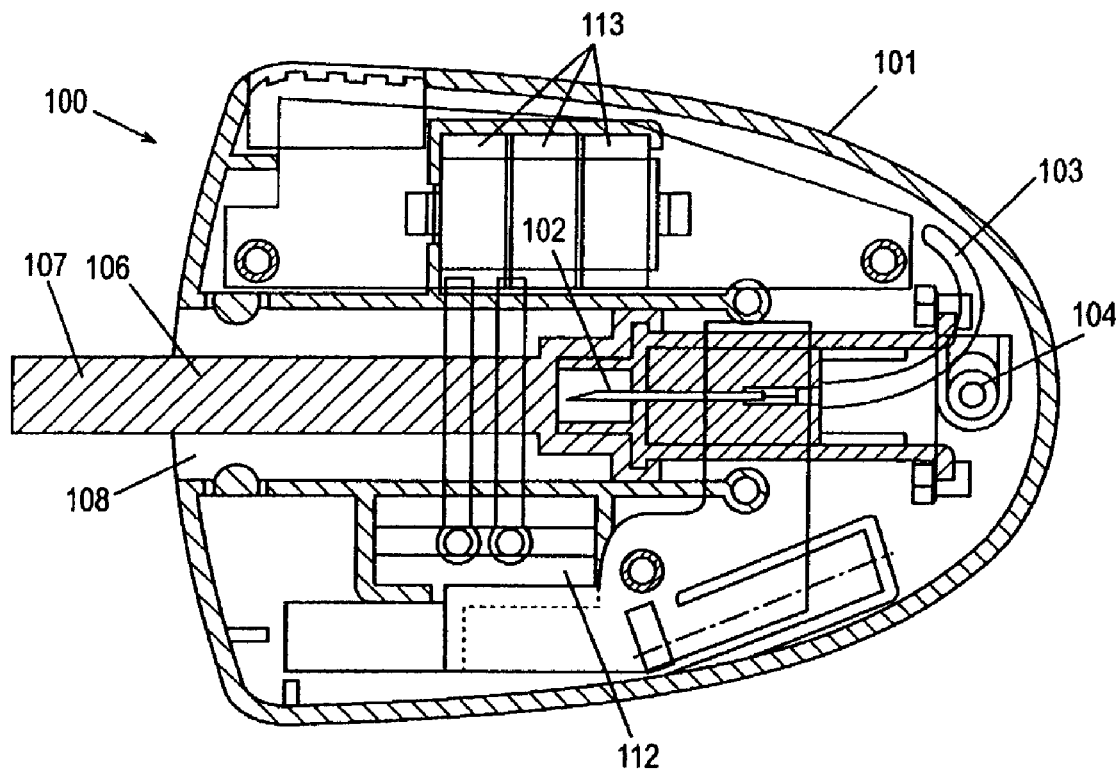
FIG. 18 is a sectional plan view of a fifth embodiment of a drug delivery device according to the invention.
Figure 19:
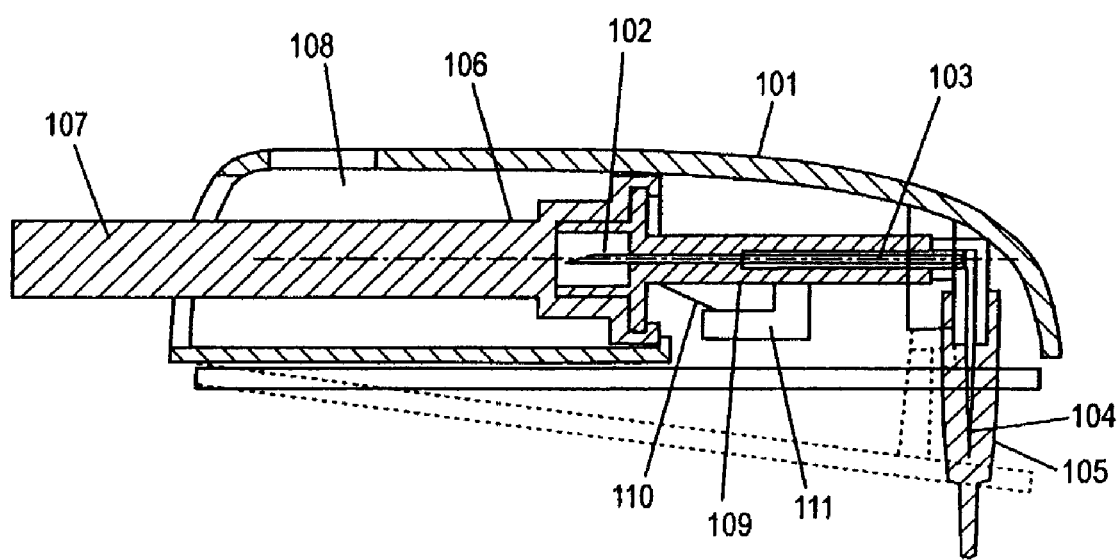
FIG. 19 is a sectional side view of the embodiment of FIG. 18.

A further alternative embodiment is illustrated in FIG. 18. The device, indicated generally at 100, has a housing 101 containing an internal needle 102 connected via a length of flexible tubing 103 to a delivery needle 104 (seen in sectional side view in FIG. 19). As with previously illustrated embodiments, delivery needle 104 is protected by a sheath 105 before use. Internal needle 102 is also protected by a sheath 106 which is provided with a tab 107 extending the length of an internal bore 108 to the exterior of the housing 101.

Flexible tubing 103 is carried on a ratchet bar 109 which can be driven to move the internal needle 102 in the direction of the internal bore 108. It can be seen from FIG. 19 that a leaf spring 110 acting as a pawl is carried on a lever 111 to drive the ratchet bar in the manner previously described. Referring back to FIG. 18, the lever 11 is driven by the expansion and contraction of an electrolytic cell 112 which is powered by batteries 113.

Figure 20:
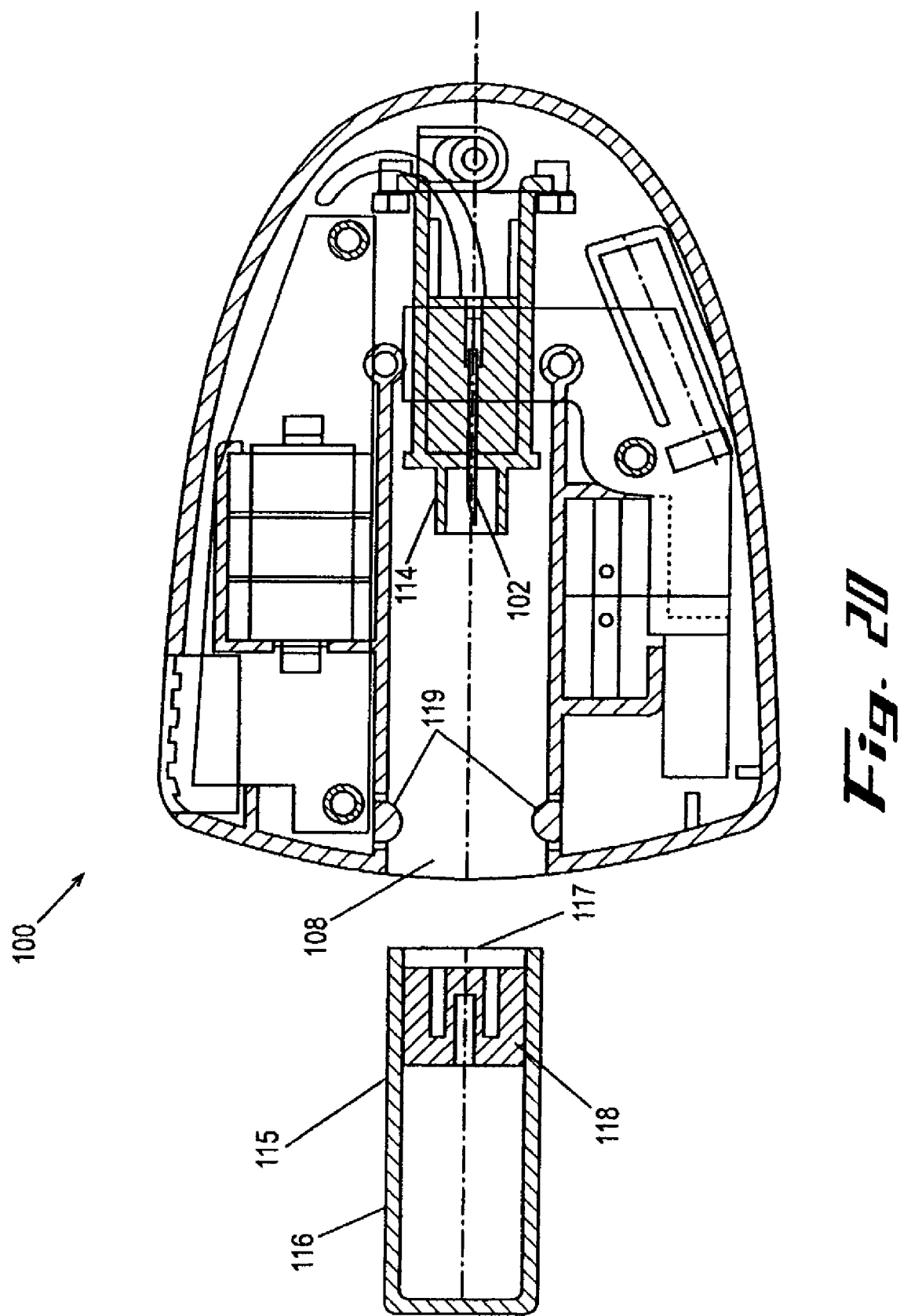
FIG. 20 is a sectional plan view of the embodiment of FIG. 18, as it is being prepared for use.

FIG. 20 shows a step in the preparation of device 100 for use. The internal sheath 106 has been removed and is no longer visible, thereby exposing internal needle which is in the centre of a cylindrical cup 114. A drug cartridge 115 is provided in the form of a cylindrical container 116 sealed at its open end 117 by a piston 118 slidably received in the container 116. Bore 108 is dimensioned to receive cartridge 115, and a pair of resilient projections 119 inside the bore 108 hold the cartridge in place when it is pushed home within the bore.

Figure 21:
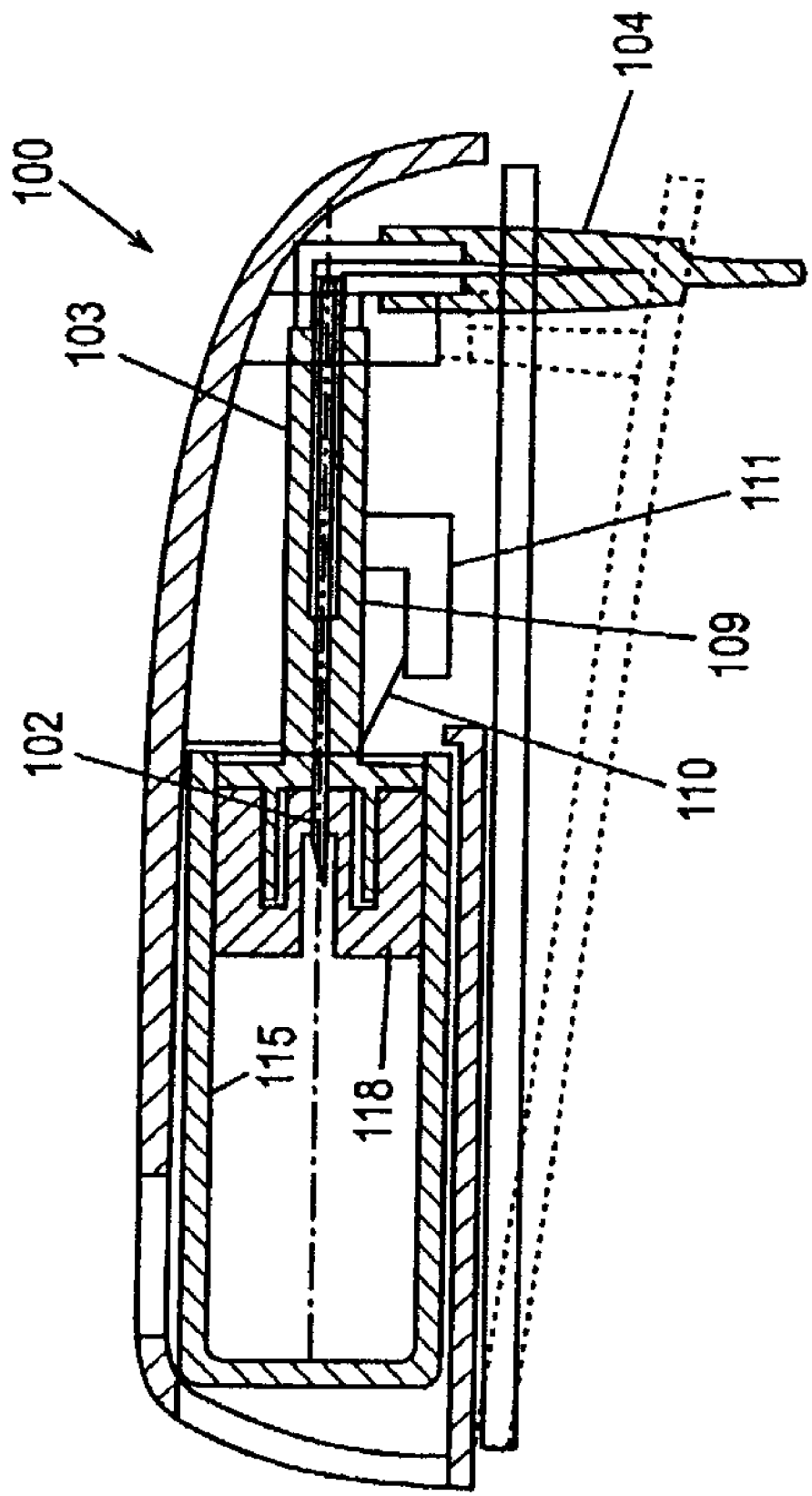
FIG. 21 is a sectional side view of the embodiment of FIG. 18 when ready for use.

FIG. 21 shows the device 100 when the cartridge 115 has been pushed home. Internal needle 102 penetrates piston 118, such that the internal needle 102 is in fluid communication with the drug inside the cartridge 115. Thus, movement of the ratchet bar 109 into the cartridge 115 causes the piston 118 to be pushed along the length of the cartridge 115, and thereby pump drug through the internal needle 102 and flexible tubing 103 to the delivery needle 104. As the internal needle 102 moves with the piston into the cartridge 115, the flexible tubing 103 is pulled behind, thereby maintaining communication between internal needle 102 and delivery needle 104.

Another advantage of flexible tubing 103 is that it enables delivery needle 104 to be mounted at any point on the device, and thus the placement of the delivery needle in this embodiment is not constrained by the design of the other features.

Although the electrolytic cell 112 in device 100 operates in exactly the same manner as the cells in previously described embodiments, the configuration of lever 111 and the pivot 119 on which it is mounted causes pawl 110 to advance ratchet bar 109 during the gas generation step rather than during the venting step.

Figure 22:
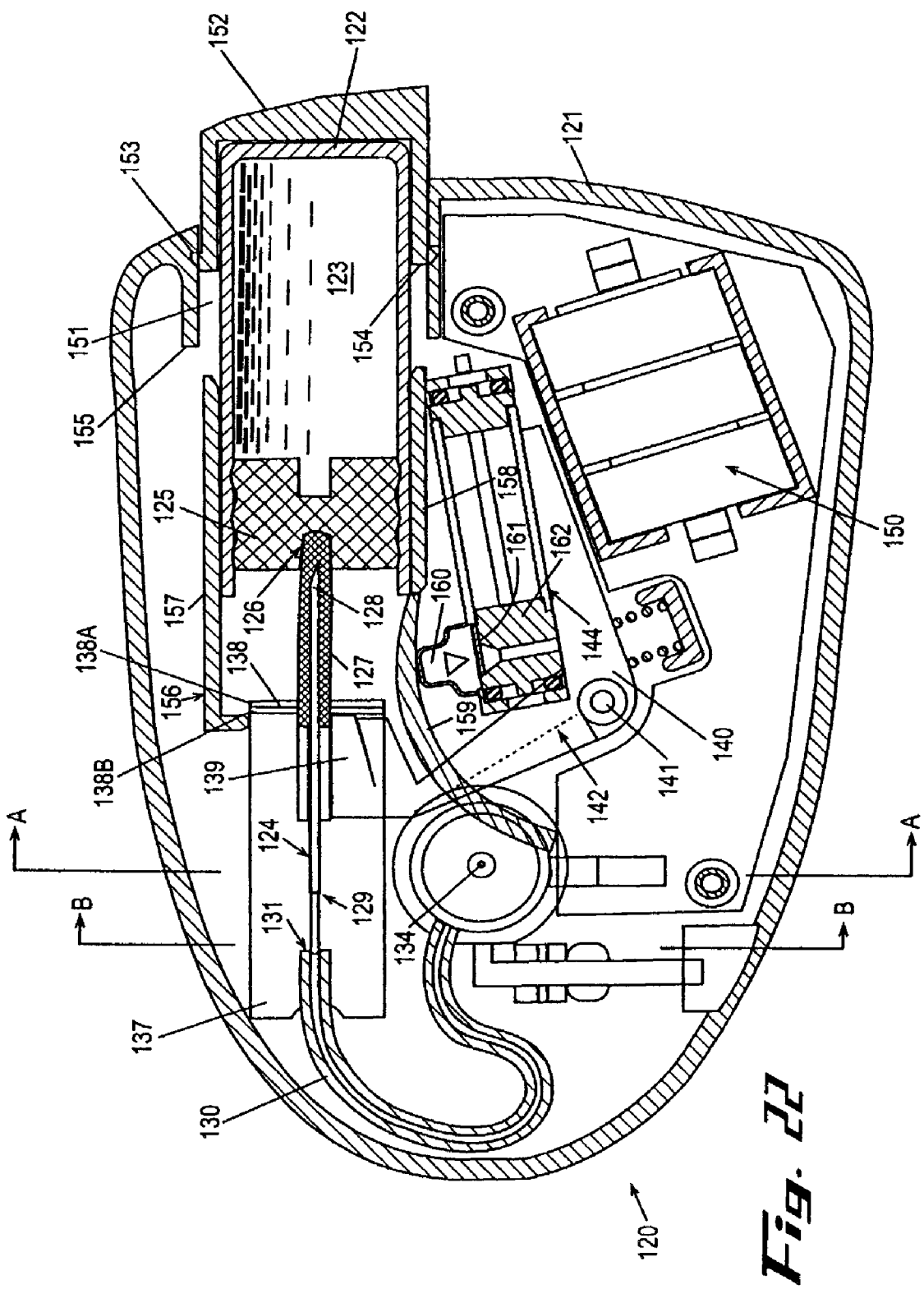
FIG. 22 is a sectional plan view of a sixth embodiment of the drug delivery device according to the invention.
Figure 22:
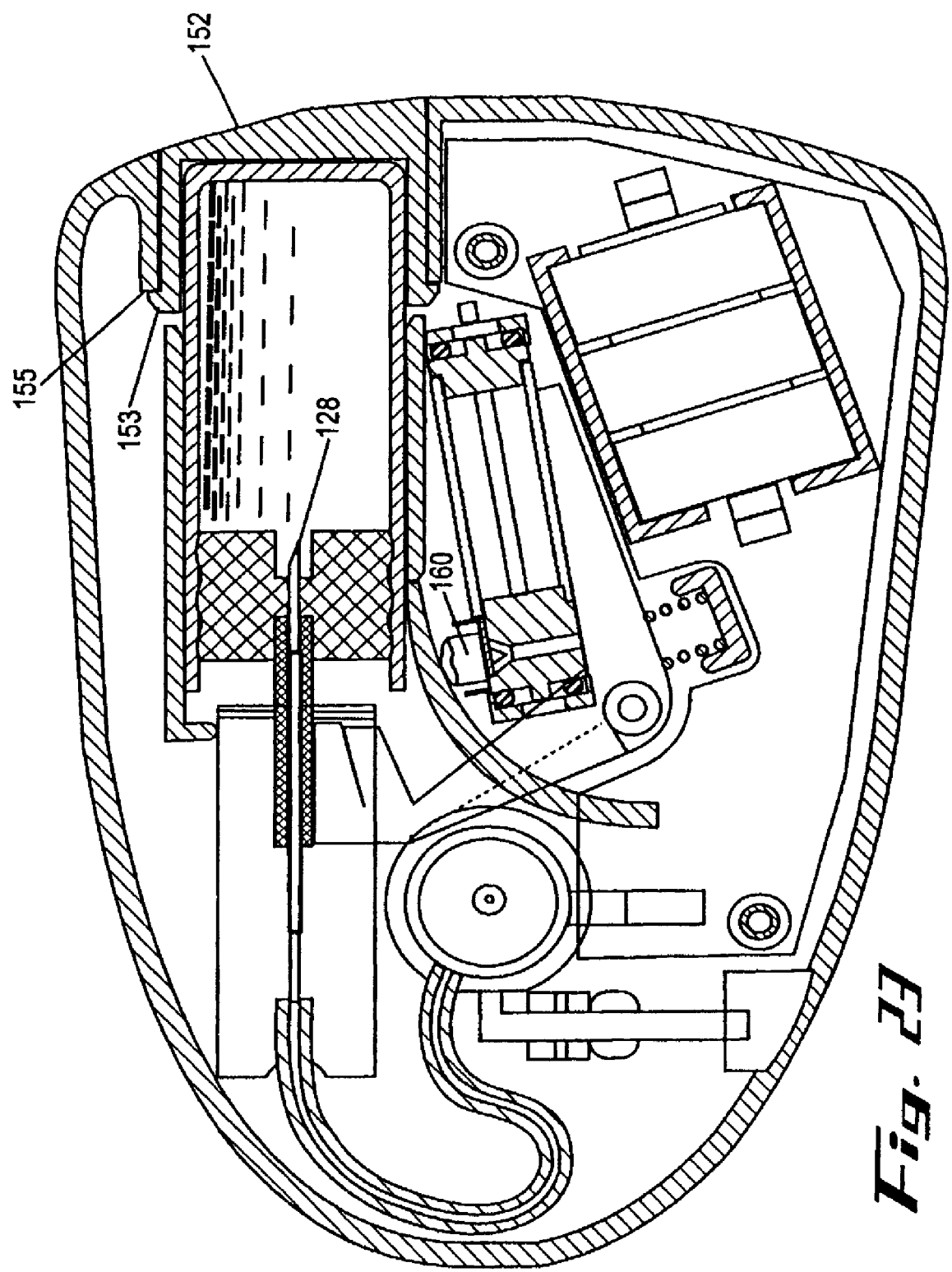
Figure 24:
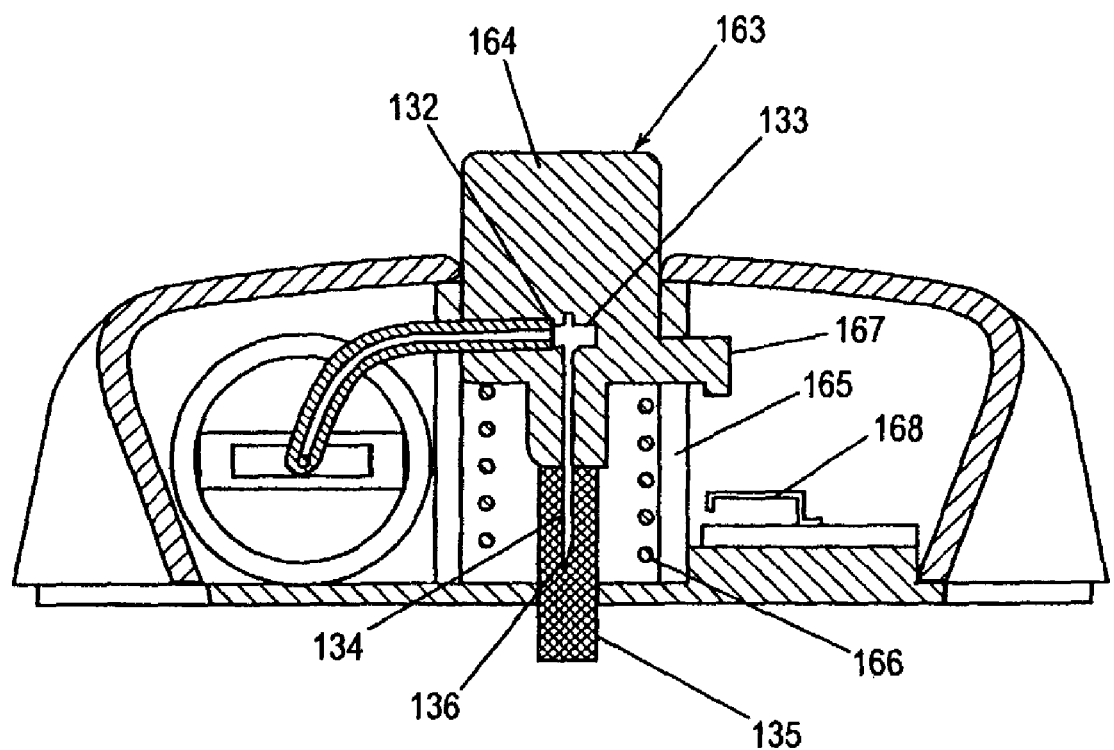
FIG. 24 is a cross-sectional view along line A-A of the embodiment of FIG. 22.

A further embodiment is shown in FIGS. 22-26. In FIG. 22, the embodiment 120 comprises a housing 121 containing a cartridge 122 filled with a drug 123. The cartridge 122 is provided with a needle 124 for delivery of drug 123 to a patient. The cartridge 122 includes a piston 125 which is slidably received in the cartridge 122. The piston has an outer recess 126 for receiving a needle sterility cover 127. The needle sterility cover 127 covers a first end 128 of the needle 124 and prevents contamination thereto. A second end 129 of the needle 124 is connected to a length of tubing 130. The tubing 130 has a first end 131 and a second end 132, as shown in FIG. 24. The tubing 130 second end 132 is secured within an activation assembly 163. A second needle 134 is also secured to the activation assembly 163. A drug pathway 133 is machined into the activation assembly 163, and the tubing 130 and second needle are secured within the activation assembly by means of an adhesive, preferably an ultra-violet bonding agent. A second needle sterility cover 135 is slidably received on the exterior end 136 of the second needle 134. Prior to use, the second needle sterility cover 135 is manually removed so as to uncover the exterior end 136 of the second needle 134 so that it is ready for penetration into the user's skin.

Returning now to FIG. 22, the piston 125 and needle 124 are mounted on a ratchet bar 137 having a multitude of stepped increments 138 thereon. The ratchet bar 137 is moved by a leaf spring 139 integral with a reciprocating lever 140. The lever 140 is mounted on an axis 141 and has a return spring 142 that applies constant pressure to the lever 139 in a single direction. The lever 139 rests against a gas generator sub-assembly 144 and moves in response to pressure differentiation created therein.

The gas generation sub-assembly 144, includes a pair of electrolytic cells 145, 146, as shown in FIG. 26. The first cell 145 is the propulsion cell. The propulsion cell 145 has a first diaphragm 147 made of a low permeability material, such as bromo-butyl, ethylene propylene, or EPDM. The lever 140 rests against the first diaphragm 147. The second cell 146 has a second diaphragm 148 thereon. The second diaphragm 148 is made of a high permeability material, such as silicone rubber. The first cell 145 has a hose 149 extending from the side of the first cell 145 to above the surface of the top of the second cell 146. A gap 143 is created between the end of the hose 149 and the top surface of the second cell 146. The cells 145, 146 are activated with electrical energy from batteries 150.

Additional components in the present embodiment 120 include a drug cartridge recess 151, as shown in FIG. 23. The drug cartridge has a sleeve 152 for receiving and supporting the cartridge 122 and ensuring safe and accurate operation of the device 120. The sleeve 152 is slidably received into the recess 151. The sleeve 152 has a lip 153 on the exterior at the insertion end 154 of the sleeve. The recess 151 has a shelf 155 for receiving the lip 153 of the sleeve when the cartridge 122 is fully inserted, as shown in FIG. 21. A cartridge receiving channel 156 is located within the housing 121 and is proximate to the recess 151. The channel provides further support for the cartridge when it is inserted within the device 120. The channel includes an outer edge 157, an inner edge 158 and an arched portion 159. The outer and inner edges are parallel and align with the cartridge recess to guide and support the cartridge 122 upon insertion and during use. The arched portion 159 of the channel is integral with the inner edge 158 and is curved away from the cartridge and ratchet assembly. Prior to operation, the arched portion 159 rests against a depressable button 160 that is part of the gas generating sub-assembly 137. The button 160 has a puncturing device on the inner surface thereof. When depressed, the puncturing mechanism breaks a seal 161 of the compartment 162 containing the chemical entity used in the electrolytic cells 145, 146 of the gas generating sub-assembly 144, as shown in FIG. 22. The chemical entity is typically potassium chloride, and in the present embodiment, it is preferably in a less viscous form so as to enable the liquid to move to gaseous form more quickly.

With this design, in the event the electrical connection is made prior to use, gas generation in the sub-assembly 144 is not possible because the gas generating chemical is sealed within its compartment 162. In addition, this design prevents operation of the device unless the drug cartridge is fully engaged. The arched portion 159 is located so as to only be deflectable by the drug cartridge when the cartridge is in its fully inserted position. Thus, ensuring that the full dosage of the drug will be delivered.

Figure 25:
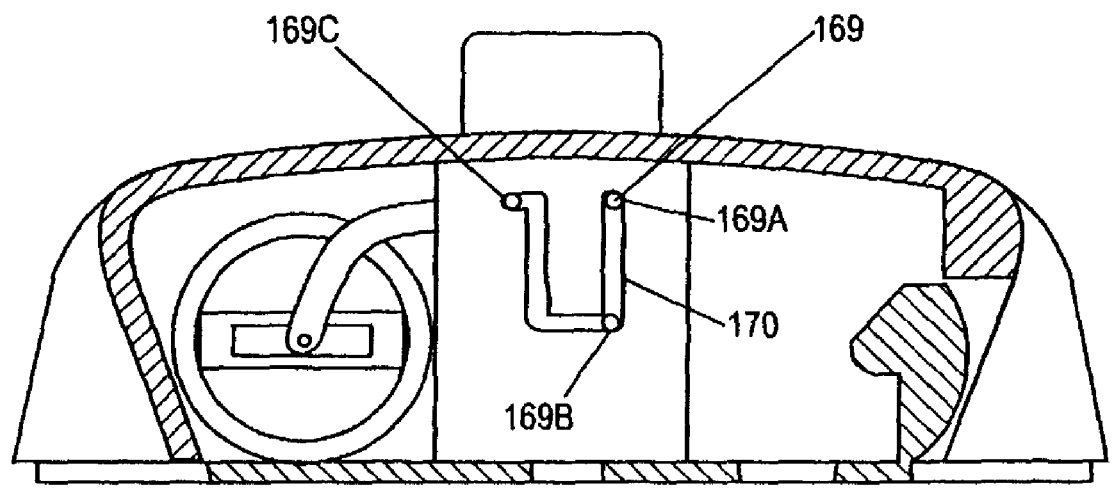
FIG. 25 is a cross-sectional view along line B-B of the embodiment of FIG. 22.

FIG. 24 shows a cross-sectional view of manual activation assembly 163 along line A-A. The activation assembly 163 includes a spring loaded start button 164 which is slidably received within a button channel 165. The button 164 is maintained in an outward position by means of a helical spring 166, located and supported in the button channel 165. The helical spring 166 is loaded both axially and torsionally within the button channel 165. FIG. 25 is a cross-sectional view of the activation assembly along line B-B, which shows a pin 169 which moves within a groove 170 in the button channel 165 from a first, pre-operational position [shown as position 169A], to a second, operational position [169B], to a third, locked position [169C].

Returning to FIG. 24, the button 164 has a finger 167 extending therefrom. The finger 167 is located directly above a deflectable electrical contact 168. When the button 164 is depressed, the finger 167 contacts the electrical contact 168 and causes it to deflect, thus causing electrical communication between the contacts and initiating operation of the device 120.

In operation, the embodiment 120, shown in FIG. 22, is supplied with a drug cartridge 122. The cartridge 122, filled with drug 123 is fully inserted into the cartridge recess 151. When the cartridge 122 is fully inserted, the lip 153 of the sleeve 152 lockably engages with the shelf 155 and prevents the cartridge 122 from being removed. As the cartridge 122 is inserted, the needle sterility cover 127 engages with the piston outer recess 126, and the tip of the needle pierces the needle sterility cover 127 and piston 125 and moves into the interior of the cartridge, as shown in FIG. 23. The travel of the cartridge ends when the sleeve lip engages with the shelf and the inner and outer edges of the channel. As the cartridge is fully inserted, the cartridge edge contacts the arched portion of the channel 156 causing it to deflect away from the cartridge. Such deflection applies pressure to the depressable button which depresses and pierces the container of chemical used to generate the gas within the electrolytic cells. The device 120 is then applied by the user or health care worker to the skin.

The device is then activated when the start button 164 is depressed causing the finger 167 to contact the electrical contact 168 thus closing an electrical circuit which initiates gas generation in the sub-assembly. Once the button 164 is depressed, the torsional force of the helical spring 166 prevents the button from springing back up and locks the button, and second needle 134 in position [169B] during operation, as shown in FIG. 25.

Figure 26A:
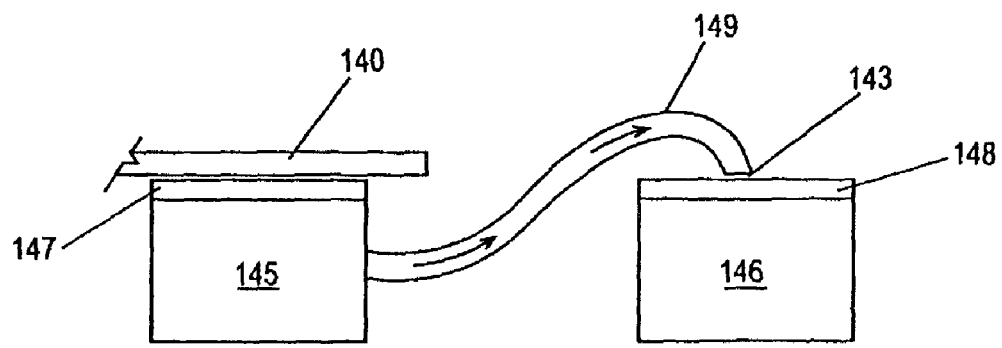
FIG. 26 is a schematic drawing representing the various parts of the gas generation sub-assembly of the embodiment of FIG. 22.
Figure 26B:
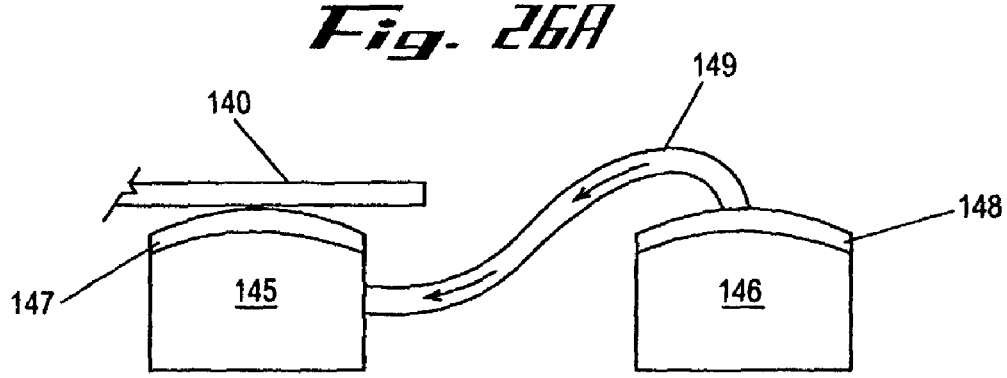
Figure 26C:
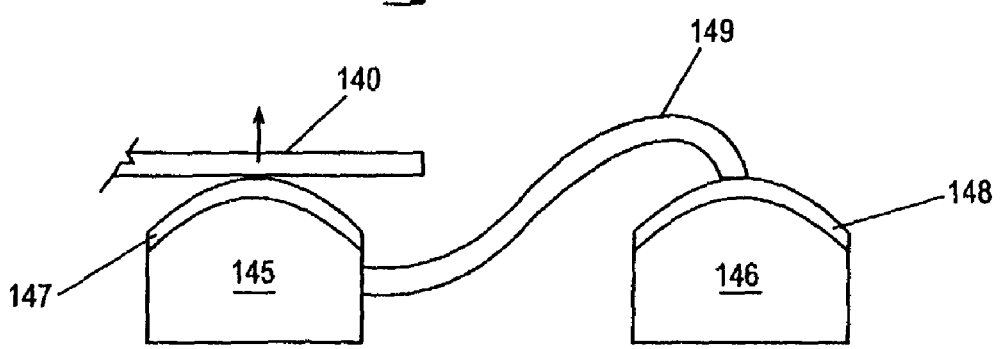

When the cells 145, 146 are activated with electrical energy from the batteries 150, both cells begin to generate gas. The first cell 145 builds pressure quickly because of the low permeability of the first diaphragm 147, as shown in FIG. 26A. However, pressure is released through the hose and exits into the atmosphere within the housing 121. As pressure builds in the second cell 146, the second diaphragm 148 deforms outwardly, closing the gap 143 between the hose and the top surface of the second cell, as shown in FIG. 26B. When this is closed, the gas from the first cell can no longer escape into the atmosphere, causing the first diaphragm to elastically deform outwardly. This deformation applies pressure to the lever 140, as shown in FIG. 26C. When pressure is applied on the lever, it causes the leaf spring to move from a first stepped increment 138A to a second increment 138B. This movement causes the piston 125 to move further along the length of the drug cartridge 122, decreasing the volume of drug 123 in the cartridge and moving such drug into the patient via the needle 124.

Figure 26D:
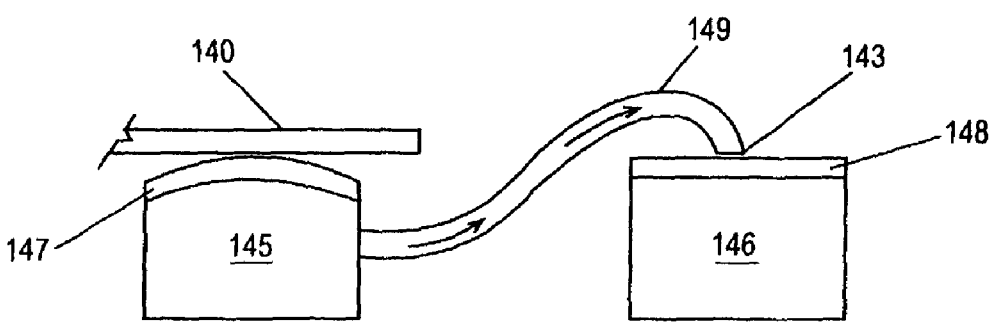

Once pressure has built sufficiently in the first cell 145 so as to move the leaf spring incrementally forward, gas generation in the cells is deactivated so as to begin to decrease pressure within the cells. As the pressure in the second cell decreases, the second diaphragm flattens out, thereby re-creating the gap 143 and allowing air to bleed quickly from the first cell, as shown in FIG. 26D.

The gas-generation sub-assembly is designed in such a way so as to provide maximum efficiency in the cycle of moving the leaf spring from a first increment 138A to a second increment 138B. The low permeability of the first diaphragm 147 allows the pressure to build in the first cell 145 and thus results in quick deformation of the diaphragm and movement of the reciprocating piston 143. However, the integration between the first and second cells, 145, 146, is important in order to quickly release the pressure within the first cell 145 after the leaf spring has been moved forward. The hose 149 between the first and second cell connects the two cells during deflection and provides first for the build up of pressure. After the pressure within the first cell builds sufficiently move the reciprocating piston, the electrical connection to the batteries 150 is disconnected, or decreased. This causes a rapid decrease in the pressure of the second cell 146 because much of the gas created escapes through the second diaphragm. As the pressure in the second cell 146 declines, the second diaphragm looses height and recreates the gap 143, thus allowing gas from the first cell to quickly bleed off and return to a low pressure state to begin the next cycle. It should be noted that it is possible to maintain a minimum current level within the cells in order to keep a minimum level of pressure in the cells so as not to start the build up of pressure from a lower point than necessary, thus maximizing the efficiency of the cycle time. In one application, the current needed during the gas generation portion of the cycle may range from 5-7 milliampers, and the current to maintain the minimum level of pressure may range from 30-50 microampers. This cell design has enabled the cycle time to decrease from 20 minutes to 5 minutes in the present embodiment.

The length between activating and deactivating the electrolytic cells may be controlled by means of a microprocessor, along with the use of different diaphragm materials. Thus, the cycle time to move the leaf spring a single increment may be adjusted depending upon the delivery rate desired. Moreover, the number and size of increments may be altered to provide further flexibility in the delivery rate.

When the delivery is complete, the helical spring 166 which is torsionally loaded, forces the pin 169 to move from the operation position [169B] to a locked post-operational position [169C]. This causes the entire activation assembly to retract and the exterior end 136 of the second needle 134 to be recessed into the housing, thereby avoiding any accidental injury or attempted further use of the device 120.

It should also be noted that in the present embodiment 120, the number of sterile components has been minimized so as to eliminate the need to sterilize the entire device. The following components are sterilized as an assembly prior to being assembled into the device. The sterilized sub-assembly includes the needle sterility cover 127, the needle 124, the tubing 130, the start button 164, the drug pathway 133, the second needle 134, and the penetrating needle sterility protector 135.

It will be appreciated that the embodiments discussed above are preferred embodiments, falling within the scope of the appended claims, and that various alternative embodiments are contemplated. For example, while leaf and coil springs were discussed in the preferred embodiments, it is anticipated that other types of springs may also be used.

The term "drug" used herein includes but is not limited to peptides or proteins, hormones, analgesics, anti-migraine agents, anti-coagulant agents, narcotic antagonists, chelating agents, anti-anginal agents, chemotherapy agents, sedatives, anti-neoplastics, prostaglandins, antidiuretic agents, anti-sense agents, oligonucleotides, mucosal vaccines, gene-based medicines and permeability and enhancing agents.

Typical drugs include peptides, proteins or hormones such as insulin, calcitonin, calcitonin gene regulating protein, atrial natriuretic protein, colony stimulating factor, betaseron, erythropoietin (EPO), interferons such as α, β or γ interferon, somatropin, somatotropin, somastostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues thereof; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues therof; anti-coagulant agents such as heparin, hirudin, and analogues therof; anti-emetic agents such as scopolamine, ondansetron, domperidone, metoclopramide, and analogues thereof; cardiovascular agents, anti-hypertensive agents and vasodilators such as diltiazem, clonidine, nifedipine, verapamil, isosorbide-5-mononitrate, organic nitrates, agents used in treatment of heart disorders, and analogues thereof; sedatives such as benzodiazepines, phenothiozines, and analogues thereof; chelating agents such as deferoxamine, and analogues thereof; anti-diuretic agents such as desmopressin, vasopressin, and analogues thereof; anti-anginal agents such as nitroglycerine, and analogues thereof; anti-neoplastics such as fluorouracil, bleomycin, and analogues thereof; prostaglandins and analogues thereof; and chemotherapy agents such as vincristine, and analogues thereof.

Other drugs include antiulcer agents, such as but not limited to cimetidine, and ranitidine; antibiotics; anticonvulsants; antiinflammatories; antifungals; antipsychotics; corticosteroids; immunosuppressants; electrolytes; nutritional agents and vitamins; general anesthetics; antianxiety agents, such as but not limited to compazine; and diagnostic agents.

What is claimed is:

1. A drug delivery device comprising:
   (a) a housing containing a drug reservoir;
   (b) means for expelling drug from the drug reservoir;
   (c) a ratchet mechanism in communication with the expelling means, the ratchet mechanism being operable to undergo incremental advancement and thereby drive the drug from the reservoir in a series of fixed increments, wherein the ratchet mechanism comprises a helical spring having coils, and one or more fingers which make a ratcheting engagement with the coils of the spring;
   (d) a member operatively associated with the ratchet mechanism to cause the incremental advancement of said ratchet mechanism as the member moves in a first direction; and
   (e) a delivery mechanism located within the housing and operable to expand a chamber, the member being in transmission relation to the chamber, whereby the member is driven by the movement of the chamber to advance the delivery helical spring and thereby drive the drug from the reservoir in the series of fixed increments, each of the fixed increments corresponding to a respective advancement of the ratchet mechanism.

2. The drug delivery device according to claim 1, wherein the helical spring is caused to advance as the chamber undergoes expansion.

3. The drug delivery device according to claim 1, wherein one or more fixed fingers are mounted in fixed position relative to the housing, and one or more reciprocable fingers are mounted on the ratchet mechanism, such that when the one or more reciprocable fingers move in a first direction they engage the coils of the helical spring to drive the helical spring in the first direction, and when the one or more reciprocable fingers move in an opposite direction, the one or more fixed fingers engage with and hold the coils of the helical spring preventing it being driven back in a second direction, whereby the fixed and reciprocable fingers co-operate to drive the helical spring in one direction only.

4. The drug delivery device according to claim 3, wherein one or each of said one or more fixed fingers is inclined in the first direction.

5. The drug delivery device according to claim 3, wherein the position of the one or more fixed fingers relative to the one or more reciprocable fingers is such that the helical spring is driven by the reciprocable fingers towards the fixed fingers.

6. The drug delivery device according to claim 3, wherein the minimum distance between the fixed and reciprocable fingers, respectively, is not greater than ten times the distance between adjacent coils of the helical spring when the helical spring is in a relaxed position.

7. The drug delivery device according to claim 6, wherein the minimum distance between the fixed and reciprocable fingers, respectively, is not greater than five times the distance between adjacent coils of the helical spring when the helical spring is in a relaxed position.

8. The drug delivery device according to claim 7, wherein the minimum distance between the fixed and reciprocable fingers, respectively, is not greater than twice the distance between adjacent coils of the helical spring when the helical spring is in a relaxed position.

9. The drug delivery device according to claim 8, wherein the minimum distance between the fixed and reciprocable fingers, respectively, is approximately equal to the distance between adjacent coils of the helical spring when the helical spring is in a relaxed position.

10. The drug delivery device according to claim 1, wherein the expelling means comprises a piston.

11. The drug delivery device according to claim 1, wherein the delivery mechanism comprises a gas generator.

* * * * *

UNITED STATES PATENT AND TRADEMARK OFFICE
CERTIFICATE OF CORRECTION

Page 1 of 1

PATENT NO. : 7,998,117 B2
APPLICATION NO. : 12/121545
DATED : August 16, 2011
INVENTOR(S) : Joseph Gross et al.

It is certified that error appears in the above-identified patent and that said Letters Patent is hereby corrected as shown below:

In the Claims:
Claim 1:
At column 20, line 5, please delete "delivery".

Signed and Sealed this
Seventh Day of October, 2014

Michelle K. Lee
*Deputy Director of the United States Patent and Trademark Office*